(12) United States Patent
Butters et al.

(10) Patent No.: US 8,076,481 B2
(45) Date of Patent: Dec. 13, 2011

(54) CHEMICAL PROCESS 632

(75) Inventors: Michael Butters, Bristol (GB); Jeffrey Crabb, Bristol (GB); Philip Hopes, Bristol (GB); Bharti Patel, Bristol (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/705,711

(22) Filed: Feb. 15, 2010

(65) Prior Publication Data

US 2010/0210841 A1 Aug. 19, 2010

(30) Foreign Application Priority Data

Feb. 13, 2009 (GB) .................................. 0902434.0

(51) Int. Cl.
*C07D 241/02* (2006.01)
(52) U.S. Cl. ........................ 544/408; 548/953
(58) Field of Classification Search .................. 544/408; 548/953
See application file for complete search history.

(56) References Cited

U.S. PATENT DOCUMENTS

| | | | |
|---|---|---|---|
| 2,750,393 A | 6/1956 | Elpern |
| 2,967,194 A | 1/1961 | Murray Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,390,908 B2 | 6/2008 | Boyd et al. |
| 7,524,957 B2 | 4/2009 | Boyd et al. |
| 7,642,259 B2 | 1/2010 | McKerrecher et al. |
| 7,642,263 B2 | 1/2010 | McKerrecher et al. |
| 7,671,060 B2 | 3/2010 | Martin et al. |
| 7,696,191 B2 | 4/2010 | McCabe et al. |
| 7,700,640 B2 | 4/2010 | Cornwall et al. |
| 7,745,475 B2 | 6/2010 | Johnstone et al. |
| 7,842,694 B2 | 11/2010 | McKerrecher et al. |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |

(Continued)

FOREIGN PATENT DOCUMENTS

CA 2605738 11/2006

(Continued)

OTHER PUBLICATIONS

Alvarez et al. "Evidence that glucokinase regulatory protein is expressed and interacts with glucokinase in rat brain" J. Neurochem. 80(1):45-53 (2002).

(Continued)

*Primary Examiner* — James O Wilson
*Assistant Examiner* — Douglas M Willis
(74) *Attorney, Agent, or Firm* — Morgan Lewis & Bockius LLP

(57) ABSTRACT

A process for preparing pharmaceutically active compounds of formula (I) or a salt thereof

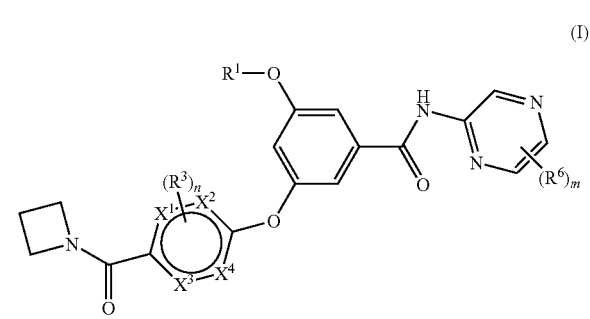

(I)

wherein $R^1$, n, m, $R^3$, $R^6$, $X^1$, $X^2$, $X^3$ and $X^4$ are as defined in the specification, is described. Novel intermediates are also described and claimed.

3 Claims, No Drawings

U.S. PATENT DOCUMENTS

| | | |
|---|---|---|
| 2003/0228982 A1 | 12/2003 | Helmke et al. |
| 2004/0014968 A1 | 1/2004 | Bizzarro et al. |
| 2004/0077555 A1 | 4/2004 | Ishihara et al. |
| 2004/0214868 A1 | 10/2004 | Hayter et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0058353 A1 | 3/2006 | McKerrecher et al. |
| 2006/0167053 A1 | 7/2006 | Iino et al. |
| 2006/0178399 A1 | 8/2006 | Nishizawa et al. |
| 2006/0258728 A1 | 11/2006 | Tani et al. |
| 2007/0078168 A1 | 4/2007 | Caulkett |
| 2007/0093535 A1 | 4/2007 | Hayter et al. |
| 2007/0112040 A1 | 5/2007 | Hayter et al. |
| 2007/0255062 A1 | 11/2007 | Johnstone et al. |
| 2007/0287693 A1 | 12/2007 | Johnstone et al. |
| 2008/0015203 A1 | 1/2008 | Johnstone et al. |
| 2008/0057074 A1 | 3/2008 | Takaoka et al. |
| 2008/0153800 A1 | 6/2008 | McCabe et al. |
| 2008/0171734 A1 | 7/2008 | Campbell et al. |
| 2008/0200694 A1 | 8/2008 | Cornwall et al. |
| 2008/0234273 A1 | 9/2008 | McKerrecher et al. |
| 2008/0280872 A1 | 11/2008 | Johnstone et al. |
| 2008/0280874 A1 | 11/2008 | Johnstone et al. |
| 2008/0300412 A1 | 12/2008 | Hopes et al. |
| 2008/0312207 A1 | 12/2008 | Johnstone et al. |
| 2008/0318968 A1 | 12/2008 | Martin et al. |
| 2009/0018157 A1 | 1/2009 | Johnstone et al. |
| 2009/0029905 A1 | 1/2009 | McKerrecher et al. |
| 2009/0062351 A1 | 3/2009 | Caulkett et al. |
| 2009/0105214 A1 | 4/2009 | McKerrecher et al. |
| 2009/0105263 A1 | 4/2009 | Caulkett et al. |
| 2009/0111790 A1 | 4/2009 | McKerrecher et al. |
| 2009/0118159 A1 | 5/2009 | McKerrecher et al. |
| 2009/0131403 A1 | 5/2009 | Kusuda et al. |
| 2009/0227592 A1 | 9/2009 | Boyd et al. |
| 2009/0253676 A1 | 10/2009 | Johnstone et al. |
| 2009/0264336 A1 | 10/2009 | McKerrecher et al. |
| 2010/0093757 A1 | 4/2010 | Bennett et al. |
| 2010/0094009 A1 | 4/2010 | McCabe et al. |
| 2010/0210621 A1 | 8/2010 | Bowden et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1790637 | 5/2005 |
| EP | 1541563 | 6/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |

| WO | WO 02/51831 | 7/2002 |
| WO | WO 02/64545 | 8/2002 |
| WO | WO 02/79145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004080966 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/105637 | 9/2007 |
| WO | WO 2007105637 | 9/2007 |
| WO | WO 2008/050101 | 5/2008 |
| WO | WO 2008/050117 | 5/2008 |
| WO | WO 2008/075073 | 6/2008 |
| WO | WO 2008148832 | 12/2008 |

OTHER PUBLICATIONS

Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the pyrido[2,3-d]pyrimidine series" J. Org. Chem. 42(6):993-996 (1977).
Ando et al. "Fluoride salts on alumina as reagents for alkylation of phenols and alcohols" Bull. Chem. Soc. Jpn. 55(8):2504-2507 (1982).
Atwell et al. "Potential antitumor agents. VI. Bisquaternary salts" J. Med. Chem. 11(2):295-300 (1968).
Baker et al. "Structure and synthesis of Pallescansin E utilising a modified Wadsworth-Emmons reaction" J. Chem. Soc., Perkin Trans. 1, 12:3087-3091 (1981).
Baker et al. "Synthesis of Pallescensin-E: Use of crown ether in the Wadsworth procedure for olefin formation" Tetrahedron Letters 22:161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994) [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42(22):3514-3518 (1977).
Berl et al. "Induced fit selection of a barbiturate receptor from a dynamic structural and conformational/ configurational library" European J. Org. Chem. (11):3089-3094 (1999).
Berl et al. "Template-induced and molecular recognition directed hierarchical generation of supramolecular assemblies from molecular strands" Chem. Eur. J. 6(11):1938-1946 (2000).
Bonina et al. "Synthesis and pharmacologic activity of 2-arylethenylthiazol-4-acetic and 4-carboxylic acids" II Farmaco 40(11):875-884 (1985).
Boucherle et al. "Recherches dans la serie des cetones polyphenoliques IV. Thiazoles" Chimica. Therapeutica. 3(5):360-363 (1968).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caira "Crystalline polymorphism of organic compounds" Topics in Current Chemistry 198:163-208 (1998).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978).
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo—and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract Number: 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract Number: 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Leighton, "Pre-clinical disease models—challenges and success stories"44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957).

Lith, "Evaluation of the effects on whole body glucose metabolism after single doses of X2000—A glucose lowering agent" Poster presentation, Master thesis in Pharmaceutical Bioscience, Goteborgs University (2008).

Lynch et al. "Localization of glucokinase gene expression in the rat brain" Diabetes 49(5):693-700 (2000).

Mastafanova et al. "Features of the catalytic reduction of 4-(3-oxoquinuclidy1-2-methylene)-6-methoxyquinoline and its ethyleneketal" Khimiya Geterotsiklicheskikh Soedinenii (1):86-94 (1989).

Mastafanova et al. "Synthesis and study of the antihypertensive activity of substituted N-acetylmercaptopropiony1-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial polypyridine and polypyrimidine receptors" Angewandte Chemie International Edition 39(3):551-554 (2000).

Mazik et al. "Molecular recognition of carbohydrates by artificial receptors: systematic studies towards recognition motifs for carbohydrates" Chem. Eur. J. 7(3):664-670 (2001).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 1-Apr. 28, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328 -7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).

Ralph et al. "Glucose Modulation of Glucokinase Activation by Small Molecules" Biochemistry 47(17):5028-5036 (2008).

Rivalle et al. "2,3 Disubstituted furans and pyrroles—XVIII: Synthesis annd rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Sarabu et al., "Glucokinase activators as new type 2 diabetes therapeutic agents" Expert Opinion on Therapeutic Patents 18(7):759-768 (2008).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Shorvon, "Pyrrolidone derivatives" Lancet 358(9296):1885-1892 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas".J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

West, Anthony R., "Solid State Chemistry and its Applications" Wiley, New York, pp. 358 and 365 (1988).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) (Oct. 1-4, 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Wolff, Manfred E. "Burger's Medicinal Chemistry", 5th Edition, Part I, John Wiley & Sons, pp. 975-977 (1995).

Yakushijin et al. "Intramolecular ring formation of phenyl azide and furan moieties" Chem. Pharm. Bull. 30(1):140-151 (1982).

Yakushijin et al. "Intramolecular ring formation of phenyl azide and furan" Heterocycles 12(8):1021-1026 (1979).

Yang et al. "Hypothalamic glucose sensor similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

CHEMICAL PROCESS 632

This application claims the benefit under 35 U.S.C. §119 (a-d) of Application No. 0902434.0 (GB) filed on 13 Feb. 2009.

The present invention relates to a process for the preparation of benzoyl amino heterocyclyl compounds which are useful in therapeutic applications as well as to intermediates for use in the process as well as their preparation.

International application Number: WO03/015774 describes compounds that are useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds have utility in the treatment of Type 2 diabetes and obesity.

A sub-group of those compounds is described and claimed in patent application is WO2007/007041.

Various routes are described in these applications for the preparation of the various compounds. These include for example, routes in which acid derivatives and in particular acid chlorides are coupled to amides to form an amide link as a final step in the process.

However, certain of the compounds described in these applications include azetidine groups. Such groups are acid and base labile, and as a result, are difficult to prepare in such a manner in good yields. The problem is exacerbated when a relatively unreactive amine such as an amino pyrazine is employed. This means that "forcing" reaction conditions are required. This may become even more problematic where the azetidine is itself bonded to a relatively labile group, such as a pyrazine ring.

Furthermore, in order to ensure that the acid labile azetidine group is introduced in a final step in the process, routes which involve protecting groups such as benzyl groups (see for example Example 34b of PCT/GB2006/002471 have been employed. Removal of such protecting groups to allow introduction of the azetidine containing moiety generally requires hydrogenation steps, which are expensive and time consuming if effected on a manufacturing scale.

According to the present invention there is provided a process for preparing a compound of formula (I) or a salt thereof

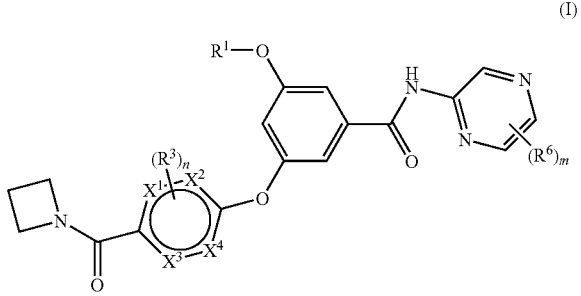

wherein
$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-tert-butoxyprop-2-yl;

each of $X^1$, $X^2$ and $X^3$ is independently selected from CH, N, S and O;
$X^4$ is absent (to make a 5-membered ring) or is selected from CH, N, O and S;
provided that at least one of $X^1$, $X^2$, $X^3$ and $X^4$ is CH and provided that there are no O—O, O—S or S—S bonds within the ring;
n is 0, 1 or 2
m is 0, 1 or 2
each $R^3$, if present, is independently selected from methyl, trifluoromethyl and halo,
each $R^6$ is present is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl, which process comprises coupling a compound of formula (II) or an activated derivative or (1-6C)alkyl ester thereof,

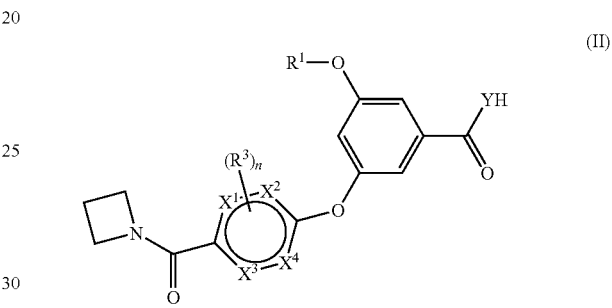

where n, $R^1$, $R^3$, $X^1$, $X^2$, $X^3$ and $X^4$ are as defined in relation to formula (I), except that any reactive group is optionally protected, Y is oxygen or sulphur, with a compound of formula (III) or a salt thereof

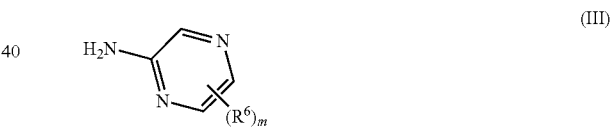

where $R^6$ and m are as defined in relation to formula (I), and thereafter if desired or necessary, removing any protecting groups and/or forming a salt of the compound of formula (I).

Suitable compounds of formula (II) are compounds are free acids or thioesters as shown or an activated derivative thereof.

Suitable salts of compounds of formula (III) are acid addition salts such trifluoroacetic acid (TFA) salt. In a particular embodiment, the compound of formula (III) is in the form of a free base.

In a particular embodiment, Y is oxygen.

The applicants have found that by controlling and selecting the coupling conditions, good yields of the compounds of formula (I) can be achieved. Many agents which act as coupling agents for the formation of amides are known and these may be used to effect the coupling of the compound of formula (II) to formula (III) to produce the amide of formula (I). Examples include for instance 2,4,6-triisopropylbenzenesulfonyl-chloride, p-toluenesulfonylchloride, 3,4,5-trifluorophenylboronic acid, 3,5-bis-(trifluoromethyl)phenylboronic acid, N,N-disuccidinylcarbonate, N,N-carbonyldiimidazole (particularly with imidazole hydrochloride as a catalyst), chlorodimethoxytriazine, and carbodiimide type coupling reagents such as 1-ethyl-3-(3'-dimethylaminopropyl)-carbodiimide (EDCI) with additives to form the activated ester such as N-hydroxy-succinimide and hydroxy benzotriazole (HOBt) etc.

In particular, the reaction is effected in the presence of a coupling agent which forms a reactive intermediate, but does not form a strong acid and/or strongly nucleophilic anion, such as iodide, as a by-product or as a component of the activating agent. In such cases the compounds of formula (I) are suitably in the form of acids rather than an activated derivative thereof.

Particular examples of coupling agents which are effective but do not significantly attack the azetidine ring include 1-propanephosphonic acid cyclic anhydride (T3P) (also known as 2,4,6-tripropyl-1,3,5-trioxatriphosphinane 2,4,6-trioxide) or 1-chloro-1-(dimethylamino)-2-methyl prop-1-ene (Ghosez reagent).

The reaction is suitably carried out in an organic solvent such as 2-methyl tetrahydrofuran, acetonitrile, ethyl acetate or dichloromethane (DCM).

Suitable reaction conditions include elevated temperatures for example from 40-100° C., conveniently at the reflux temperature of the solvent.

Suitable activated derivatives of acid (II) may include acid chlorides, anhydrides or mixed anhydrides, activated esters such as hydroxy benzotriazole (HOBt) ester and dimethoxytriazine ester.

Activated derivatives such as acid chlorides in particular are suitably prepared by reacting a salt of a compound of formula (II) in particular the sodium salt with an activating agent, such as a halogenating agent, particularly a chlorinating agent, in particular oxalyl chloride or thionyl chloride. The activated derivative may be reacted directly in situ to form the product.

Particularly the coupling agent is selected from 1-propanephosphonic acid cyclic anhydride (T3P), 1-chloro-1-(dimethylamino)-2-methyl prop-1-ene (Ghosez reagent), p-toluenesulfonyl chloride, 2,4,6-triisopropylbenzenesulfonylchloride or thionyl chloride with an excess of base.

Reaction conditions here are generally similar to those described above for the use of coupling agents such as T3P. However, in this case, it is essential to ensure that water is not allowed access to the reaction and a preliminary drying step, for example by azeotrope methods, may be applied to the starting materials.

Where an acid chloride is used in the process, the reaction is generally carried out in the presence of an excess of base particularly a basic amine such as pyridine, (4-dimethylamino)pyridine (DMAP), (4-pyrrolidino)pyridine and in particular derivatives of 3,4-diamino pyridines like 1,4-dimethyl-1,2,3,4-tetrahydropyrido[3,4-b]pyrazine, in order to avoid a ring opening reaction occurring. In particular the base is pyridine.

Where an ester of the compound of formula (II) is used in the process, the ester is suitably a lower alkyl ester such as a methyl ester. In this case however, it is preferable to include an activating agent such as trimethylaluminium or a Lewis acid in the reaction in order to "activate" the compound of formula (III).

It will be understood that the dotted circle inside the ring containing $X^1$ to $X^4$ in formula (I) and (II) is intended to indicate that the ring is aromatic, although the precise number and position of the double bonds will be dependent on the nature of $X^1$ to $X^4$. As a result, any carbon atom $X^1$, $X^2$, $X^3$ or $X^4$ will carry only one $R^3$ group.

In a particular embodiment, one or two of $X^1$, $X^2$, $X^3$ and $X^4$ are nitrogen atoms. They will not be quaternised or carry an $R^3$ substituent to the extent that this would interfere with the aromatic nature of the ring.

Where $R^3$ is present, it may be selected from chloro, fluoro or methyl, and in particular chloro.

In a particular embodiment, n is 1.

In another particular embodiment n is 0.

Thus particular examples of compounds of formula (I) are compounds of formulae (IB), (IC) and/or (ID):

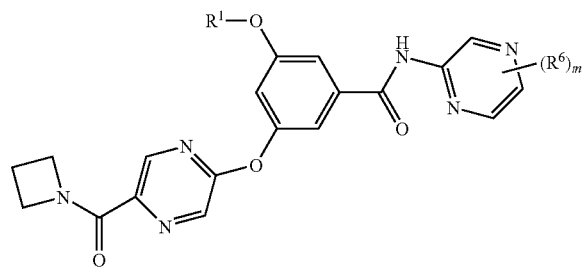

(IB)

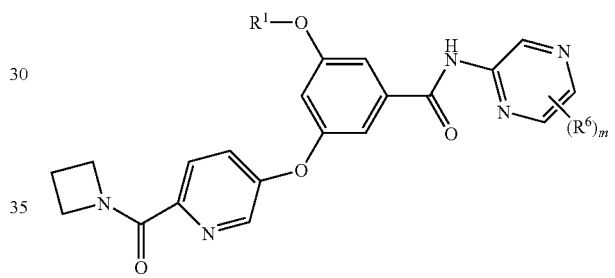

(IC)

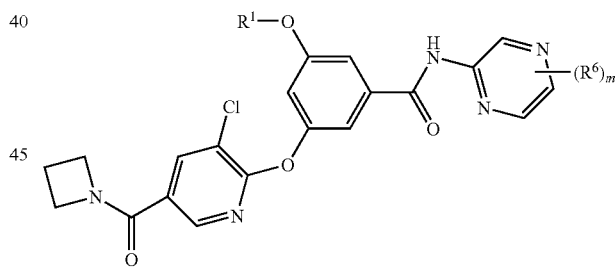

(ID)

wherein $R^1$, $R^2$, $R^6$ and m are as defined for a compound of formula (I). Compounds of formula (IB) provide a further aspect of the invention.

Particular examples for $R^1$ include isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl and 1-tert-butoxyprop-2-yl.

In another embodiment, $R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl and 1-tert-butoxyprop-2-yl.

Particular examples of $R^1$ are groups of sub-formula X:

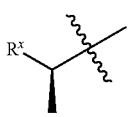
(X)

is wherein $R^x$ is selected from methyl, ethyl, trifluoromethyl, ethynyl, hydroxymethyl, hydroxyethyl, methoxymethyl, tert-butoxymethyl, fluoromethoxymethyl, difluoromethoxymethyl and trifluoromethoxymethyl; preferably $R^x$ is selected from methyl, ethyl, trifluoromethyl, ethynyl, hydroxymethyl, hydroxyethyl, methoxymethyl and tert-butoxymethyl.

In particular, $R^1$ is 1-hydroxyprop-2-yl and the configuration is preferably (S), that is $R^1$—O— is:

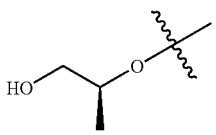

Alternatively, $R^1$ is 1-methoxyprop-2-yl and the configuration is preferably (S), that is $R^1$—O— is:

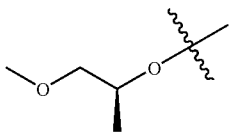

Suitably, m is 0 or 1.
In particular m is 1.
In a particular embodiment, $R^6$ is selected from (1-4C)alkyl, halo, hydroxy(1-4C)alkyl and di(1-4C)alkylamino(1-4C)alkyl. For example $R^6$ is selected from methyl, ethyl, bromo, chloro, fluoro, hydroxymethyl, methoxymethyl, aminomethyl, N-methylaminomethyl and dimethylaminomethyl.

Examples of $R^6$ include methyl, ethyl, bromo, chloro, fluoro, hydroxymethyl and methoxymethyl.

In one embodiment, $R^6$ is selected from methyl, ethyl, chloro and fluoro, in particular methyl or fluoro, and preferably methyl.

In this specification the generic term "alkyl" includes both straight-chain and branched-chain alkyl groups. Unless otherwise stated, they may contain from 1-20, suitably from 1-6 carbon atoms. Similarly, references to alkenyl or alkynyl groups refers to unsaturated groups containing for example from 2 to 20 carbon atoms. A reference to "lower" alkyl, alkenyl or alkynyl refers to groups having up to 6 and in particular up to 3 carbon atoms.

These references also apply to alkyl groups which are part of a larger moiety such as "aralkyl" (which are alkyl groups substituted with aryl groups) or alkoxy groups where the alkyl group is linked via an oxygen atom. Aryl groups are aromatic carbocyclic groups such as phenyl or napthyl.

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of halo(1-4C)alkyl include fluoromethyl, chloromethyl, fluoroethyl, chloroethyl, fluoropropyl and fluorobutyl; examples of dihalo(1-4C)alkyl include difluoromethyl, 1,1-difluoroeth-2-yl, 1,2-difluoroeth-2-yl, 1,1-dichloroeth-2-yl, 1,2-dichloroeth-2-yl, and 1,1-difluoroprop-3-yl; examples of trihalo(1-4C)alkyl include trifluoromethyl and 1,1,1-trifluoroeth-2-yl; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; example of (1-4C)alkoxy include methoxy, ehtoxy, propoxy, isopropxy, butoxy and tert-butoxy; examples of (1-4C)alkylS(O)p(1-4C)alkyl (where p is 0, 1 or 2) include methylsulfinylmethyl, ethylsulfinylmethyl, ethylsulfonylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of (1-4C)alkylsulfonyl include methylsulfonyl, ethylsulfonyl, propylsulfonyl, isopropylsulfonyl and tert-butylsulfonyl; examples of —S(O)p(1-4C)alkyl include (1-4C)alkylsulfonyl, methylsulfonyl, ethylsulfonyl, propylsulfinyl, isopropylsulfinyl, tert-butylsulfinyl, methylthio, ethylthio, propylthio, isopropylthio and tert-butylthio; examples of amino(1-4C)alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of —C(O)(1-4C)alkyl and (1-4C)alkylcarbonyl include methylcarbonyl, ethylcarbonyl, propylcarbonyl and tert-butyl carbonyl; examples of (1-4C)alkylamino include methylamino, ethylamino, propylamino, isopropylamino, butylamino and tert-butylamino; examples of di(1-4C)alkylamino include dimethylamino, diethylamino, N-methyl-N-ethylamino, dipropylamino, N-isopropyl-N-methyamino and dibutylamino; examples of (1-4C)alkylaminocarbonyl include methylaminocarbonyl, ethylaminocarbonyl, propylaminocarbonyl, isopropylaminocarbonyl, butylaminocarbonyl and tert-butylaminocarbonyl; examples of di(1-4C)alkylaminocarbonyl include dimethylaminocarbonyl, diethylaminocarbonyl, N-methyl-N-ethylaminocarbonyl, dipropylaminocarbonyl, N-isopropyl-N-methyaminocarbonyl and dibutylaminocarbonyl.

Compounds of formula (II) are suitably prepared by hydrolysis of a compound of formula (IV)

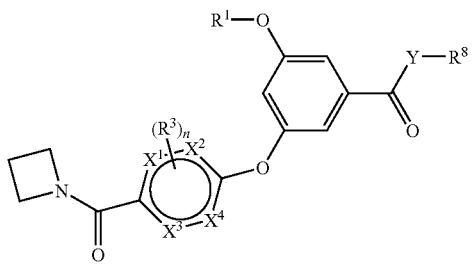 (IV)

where $R^1$, $R^3$, $X^1$, $X^2$, $X^3$ and $X^4$ and n are as defined in relation to formula (I), provided that any reactive group within the molecule is optionally protected, Y is as defined in relation to formula (II) and $R^8$ is an acid or thioester protecting group.

Suitable acid or thioester protecting groups $R^8$ would be apparent to a skilled chemist, but include for example $C_{1-6}$ alkyl such as methyl, as well as allyl, benzyl or phenyl.

Hydrolysis is suitably effected under mild conditions using for example an alkali metal hydroxide salt, such as lithium hydroxide or sodium hydroxide. The reaction is suitably effected in an organic solvent such as dimethylformamide (DMF), tetrahydrofuran (THF), N-methylpyrrolidone (NMP) or an alkyl alcohol such as methanol or ethanol. Particular solvents may be non-acidic or non-protonic such as DMF, NMP or THF. Temperatures of from $-10$ to $30°$ C., for example from 0 to $10°$ C. are suitably employed.

Compounds of formula (IV) are suitably prepared by reacting a compound of formula (V)

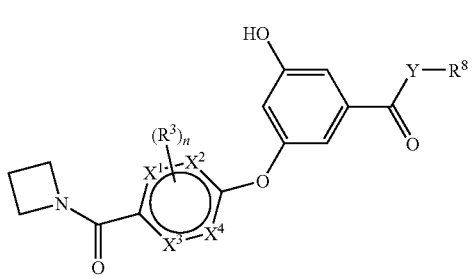 (V)

where $R^3$, $X^1$, $X^2$, $X^3$ and $X^4$ and n are as defined in relation to formula (I) and Y is as defined in relation to formula (II), except that any reactive groups are optionally protected, and $R^8$ is as defined in relation to formula (IV), with a compound of formula (VI)

$R^1$-L (VI)

where $R^1$ is as defined in relation to formula (I) and L is a leaving group.

Particular examples of leaving groups for L include tosylate and mesylate, and in particular tosylate. Further examples of leaving groups include p-nitrophenylsulfonate, p-nitrilephenylsulfonate (p-cyanophenylsulfonate), p-methanesulfonylphenylsulfonate, p-trifluorobenzene sulfonate and p-chlorophenylsulfonate.

The reaction to form (IV) from reacting (V) and (VI) is suitably carried out at elevated temperatures for example from 40-100° C., for example at about 80° C. Alternatively the reaction may be carried out at about 45° C. It is suitably effected in an organic solvent such as dimethylsulfoxide (DMSO).

Compounds of formula (V) are suitably prepared by reacting a compound of formula (VII)

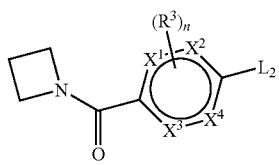 (VII)

is where $X^1$, $X^2$, $X^3$, $X^4$, $R^3$ and n are as defined in relation to formula (I) except that any reactive group is optionally protected, and $L_2$ is a leaving group, with a compound of formula (VIII)

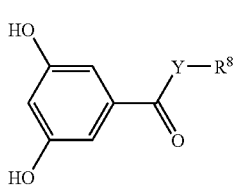 (VIII)

where Y is as defined in relation to formula (II), $R^8$ is as defined in relation to formula (IV), in the presence of a base.

Suitable bases may include alkali metal carbonates such as sodium or potassium carbonate. A particularly suitable base for use in the process is cesium carbonate, which is suitably present in a significant excess, for example at least 2.5 times the stoichiometric amount of the compound of formula (VIII) (ie at least 2.5 molar equivalents).

In some cases, in particular for example where the ring containing $X^1$, $X^2$, $X^3$ and $X^4$ is amenable to nucleophilic substitution such as a pyrazine ring, the reaction between compounds of formula (VII) and (VIII) is an equilibrium reaction and there is a problem that by-products in the form of bis-ethers may be formed. The reaction between compounds of formula (V) and (VI) is also complicated by equilibration. It has been found however that by utilising specifically an excess of cesium carbonate in the reaction, by-products of this type are minimised for both of the above reactions.

Compounds of formula (VII) are suitably present in an amount which is the same as or just less than the stoichiometric amount, for example the mole ratio of compound (VII) to compound (VIII) is suitably about 0.97:1 to 1:1 in order to further ensure that bis substitution does not occur.

The reaction is suitably effected in an organic solvent such as DMSO, at elevated temperatures, for example of from 30-70° C., for example at about 40-50° C., such as about 45° C.

Compounds of formula (VI) may be prepared by conventional methods. For instance, where L is tosylate, it may be prepared by tosylation using for example using para-toluenesulfonyl chloride of the alcohol of formula (IX)

$R^1$-YH (IX)

where $R^1$ is as defined in relation to formula (I) and Y is as defined in relation to formula (II). The reaction is carried out in an organic solvent such as toluene, in the presence of a base such as triethylamine and a catalyst such as trimethylamine hydrochloride. Suitably, the para-toluenesulfonyl chloride is added in a slight excess, for example at about 1.3-1.5 times the stoichiometric amount of the compound of formula (IX). Advantageously, the reaction is quenched by addition of an amine such as N,N-dimethylaminopropylamine or N,N-dimethyl-1,2,-ethylenediamine, in order to remove any excess tosyl chloride and aid purification. The resulting sulfonamide can then be removed from the product by washing with dilute acid.

Advantageously, a compound of formula (IV) may be prepared by sequential reaction of compounds of formulae (VIII) and (VII) and the resulting compound of formula (V) is directly reacted with compounds of formula (VI) in situ to form a compound of formula (IV) without isolation of a compound of formula (V).

Compounds of formula (VII) are suitably prepared by reacting a compound of formula (X)

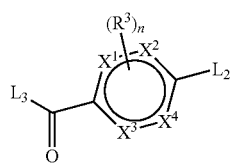

(X)

where $X^1$, $X^2$, $X^3$, $X^4$, $R^3$ and n are as defined in relation to formula (I) except that any reactive group is optionally protected, $L_2$ is as defined in relation to formula (VII) and $L_3$ is a further leaving group, which is suitably more reactive than $L_2$ such as halo and in particular chloro, with azetidine or a salt thereof. The reaction is suitably effected in an organic solvent such as DCM in the presence of a base such as triethylamine. A two-phase reaction, for example carried out in a mixture of toluene and water, in the presence such as potassium carbonate may also be used.

In a particular embodiment, the compound of formula (X) is added to a mixture of azetidine or a salt thereof, and the base, rather than the other way around, in order to is produce a higher quality product in greater yield. Suitable salts of azetidine include acid addition salts such as the hydrochloride salt. Moderate temperatures for example from −10° C. to 50° C. and conveniently between about −10° C. to −5° C. are suitably employed.

Compounds of formula (X) where $L_3$ is a halogen are suitably prepared by halogenation of the corresponding acid of formula (XI)

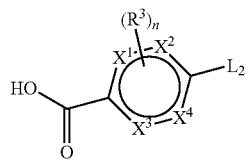

(XI)

where $X^1$, $X^2$, $X^3$, $X^4$, $R^3$ and n are as defined in relation to formula (I) except that any reactive group is optionally protected, $L_2$ is as defined in relation to formula (VII) using a halogenating agent, particularly a chlorinating agent such as oxalyl chloride or thionyl chloride. Again the reaction is suitably effected in an organic solvent such as DCM or toluene in the presence of a catalyst such as dimethylformamide (DMF) or tetrabutylammonium chloride.

Compounds of formula (XI) are suitably prepared by hydrolysis of the corresponding ester using conventional methods.

Compounds of formula (III), (VIII) and (IX) are either known compounds or they can be prepared from known compounds by conventional routes. For example, compounds of formula (III) may be prepared using a Curtius rearrangement of the corresponding carboxylic acid to an amine using conventional conditions, and for example optionally isolating urethane intermediates. Other rearrangement reactions known in the art may also be used.

In a further aspect of the invention there is provided a process for formation of a compound of formula (IIIa)

(IIIa)

comprising reaction of 5-methylpyrazine-2-carboxylic acid under conditions suitable for a Curtius rearrangement, to form a compound of formula (XII) wherein R is a) t-Bu or b) benzyl;

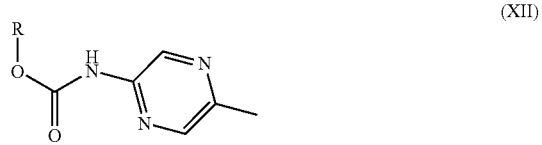

(XII)

followed by a) when R is tBu, by reaction with trifluoroacetic acid, neutralisation by base, extraction and crystallisation;

b) when R is benzyl by hydrogenation followed by catalyst removal and crystallisation.

Advantageously, R is benzyl as this affords the possibility of removal by hydrogenation in a selective, simple scaleable process. Furthermore, formation of the benzylurethane (XII) itself may be carried out by formation of the acyl azide by reaction of the dry carboxylic acid and di-isopropylethylamine with DPPA in toluene at 10 to 15° C., then addition of the acyl azide solution to a hot, dry solution of benzyl alcohol in toluene at 85 to 90° C., cooling to 20° C., addition of sodium hydroxide, and isolation by filtration to afford the product with good purity in an efficient scaleable process.

In an alternative approach, compounds of formula (II) may be made by reaction of a compound of formula (XIII)

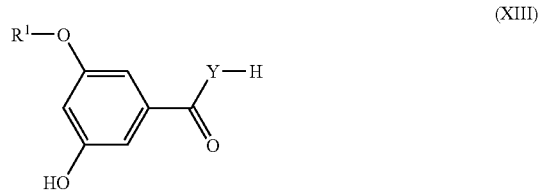

(XIII)

wherein $R^1$ and Y is oxygen, with a compound of formula (XIV)

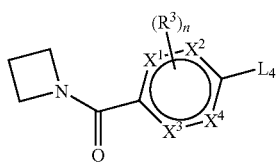

(XIV)

wherein $X^1$, $X^2$, $X^3$, $X^4$, $R^3$ and n are as defined in relation to formula (I), $L_4$ is a leaving group, such as chloro or triflate, particularly chloro.

The reaction is suitably effected in the presence of a base such as a potassium carbonate or cesium carbonate, in a polar aprotic solvent such as dimethylsulfoxide, DMF or acetonitrile. It will be appreciated that a strong base such as potassium carbonate or cesium carbonate causes double deprotonation of the compound of formula (XIII) and thereby ensures good selectivity in the reaction. The reaction is suitably carried out at an elevated temperature such as 30-80° C., such as about 45-55° C.

In a further aspect of the invention, there is provided a process for formation of a compound of formula (II) from a compound of formula (XIII) and a compound of formula (XIV) in the presence of a strong base such as potassium carbonate.

Compounds of formula (XIV) may be made as previously described for a compound of formula (VII). In particular the compound of formula (XIVa)

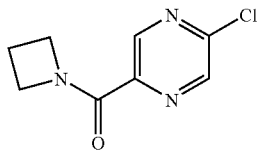

(XIVa)

may be made from a compound of formula (XIa)

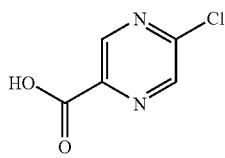

(XIa)

by reaction with a chlorinating agent such as thionyl chloride, in toluene in the presence of a catalyst for example tetra butylammonium chloride or another suitable catalyst known to those skilled in the art, followed by distillation to remove excess thionyl chloride, then addition of the acid chloride solution into azetidine or a salt thereof in a suitable solvent, for example dichloromethane or toluene or a mixture of toluene and water, and base such as potassium carbonate. After work up the product is crystallised. An optional purification of the azetidine hydrochloride may be carried out to remove the 3-chloropropylamine impurity (present in azetidine hydrochloride) by extraction of the azetidine chloride solution in water which is partially neutralised with potassium carbonate with toluene.

Compounds of formula (XIII) may be made by reaction of a compound of formula (XV)

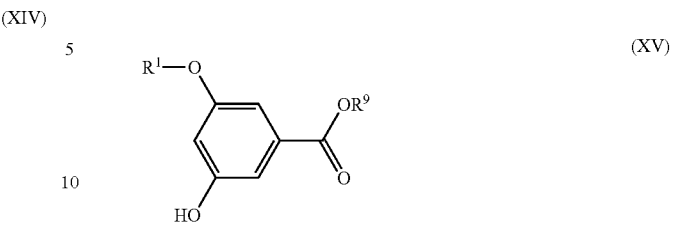

(XV)

wherein $R^9$ is suitably (1-6C)alkyl, benzyl, p-methoxybenzyl, allyl, or tert-butyl (or other suitable protecting groups known to those skilled in the art) and $R^1$ is as previously defined. Such a reaction may be carried out by conventional means known in the art, for example when $R^9$ is (1-6C)alkyl by using aqueous sodium hydroxide. It will be appreciated that the compound of formula (XIII) may be isolated as salts rather than as free acids. Such salts may be converted to the corresponding free acid by methods known in the art.

Compounds of formula (XV) may be made by de-protection of compounds of formula (XVI), wherein $P^1$ is a protecting group, for example benzoyl, p-methylbenzoyl, N,N-dimethylaminobenzoyl, tert-butylcarbonyl and isobutoxycarbonyl, or other protecting groups known in the art.

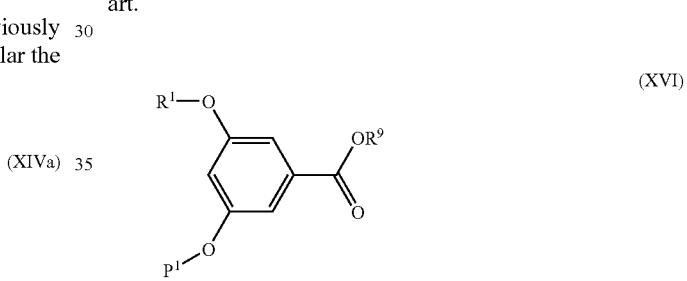

(XVI)

Such a de-protection reaction may be carried out by conventional means known in the art, for example when $P^1$ is benzoyl by treatment with refluxing sulfuric acid in methanol or alternatively by sodium methoxide in methanol. Enzymatic methods may also be used.

Compounds of formula (XVI) may be made reaction of a compound of formula (XVII) with a compound of formula (VI) as previously described. Alternatively compounds of formula (XVI) may be made reaction of a compound of formula (XVII) with a compound of formula (IX) in which Y is O using Mitsunobu conditions.

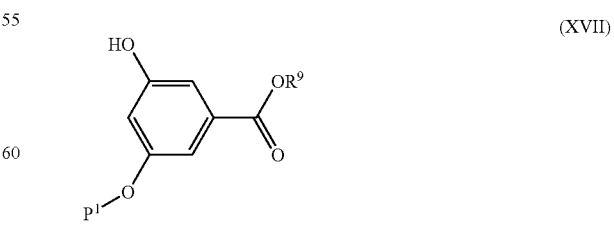

(XVII)

Compounds of formula (XVII) may be made by protection of compounds of formula (VIII) (as previously defined) under standard conditions.

Compounds of formula (XIII) may also be made from compounds of formula (XVII) via compounds of formula (XV) and (XVI) in a single telescoped process.

In a further aspect of the invention, there is provided a process for formation of a compound of formula (IV) by reaction of a compound of formula (XV) with a compound of formula (VII) in the presence of base; wherein compounds (IV), (XV) and (VII) are as hereinbefore defined.

Certain intermediates used in the processes described above are novel and these form a further aspect of the invention. In particular, the invention provides an intermediate of formula (II), (IV) (V) or (VII) as defined above. The invention further provides an intermediate of formula (XIII), (XIV) (XVI) or (XVII) as defined above.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule. The protection and deprotection of functional groups is described in 'Protective Groups in Organic Synthesis', 2nd edition, T. W. Greene and P. G. M. Wuts, Wiley-Interscience (1991).

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis. Hydrogenation may also be used.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, hydrogenation, nucleophilic displacement, acid-, base, metal- or enzymically-catalysed hydrolysis, catalytic hydrogenolysis or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid. During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

In a particular embodiment, where the compound of formula (I) is a compound where $R^1$ contains a hydroxy group, for example $R^1$ is a 1-hydroxyprop-2-yl group, the hydroxy group may be appropriately protected during one or more stages of the reaction, and the protecting group removed at a convenient stage, for example as a final step.

Particular examples of a route to a compound of formula (I) utilising the method of the invention is illustrated in Scheme 1 and Scheme 2.

Utilising the method of the invention, compounds of formula (I) may be obtained on a good scale and in good yield.

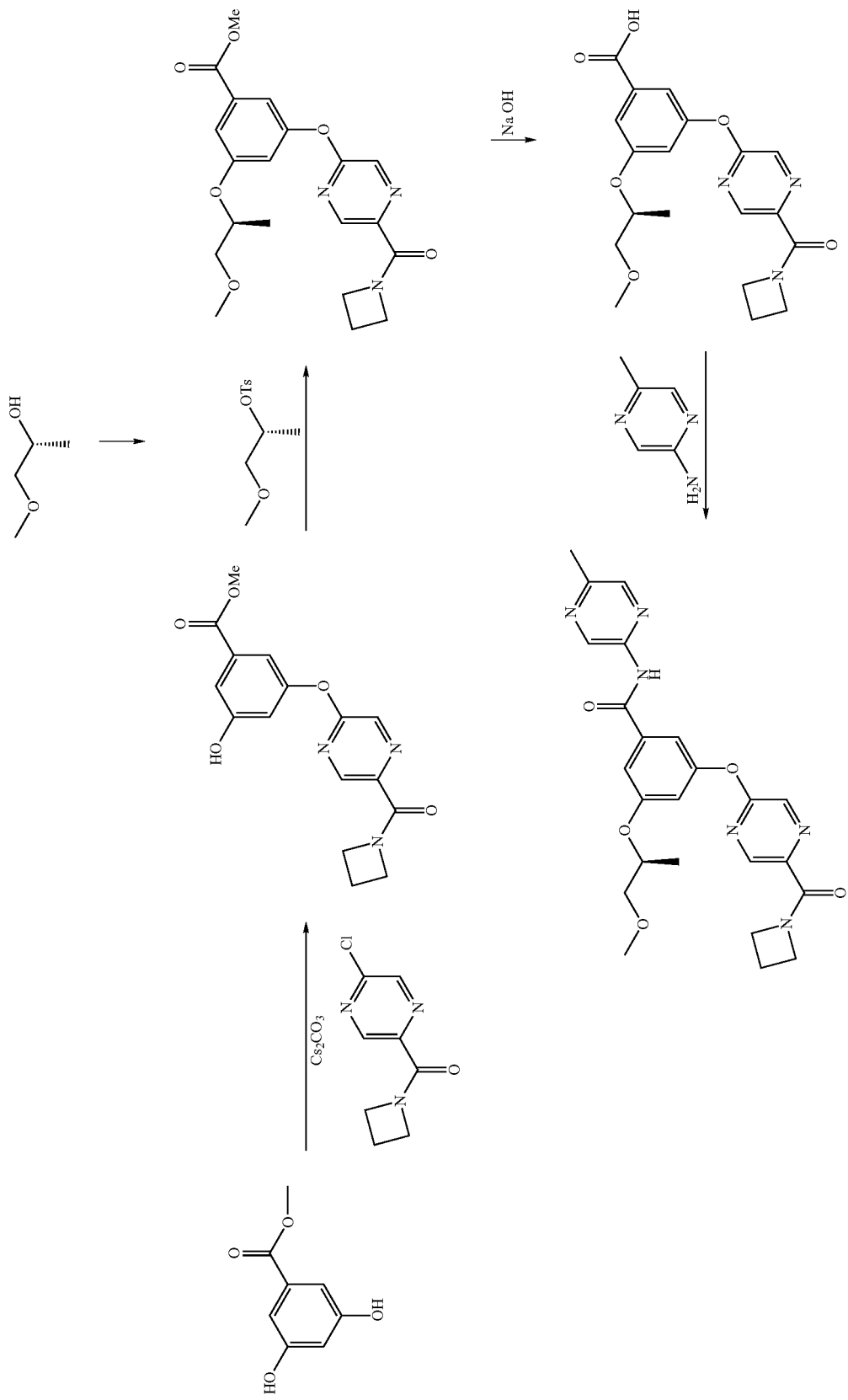
Scheme 1

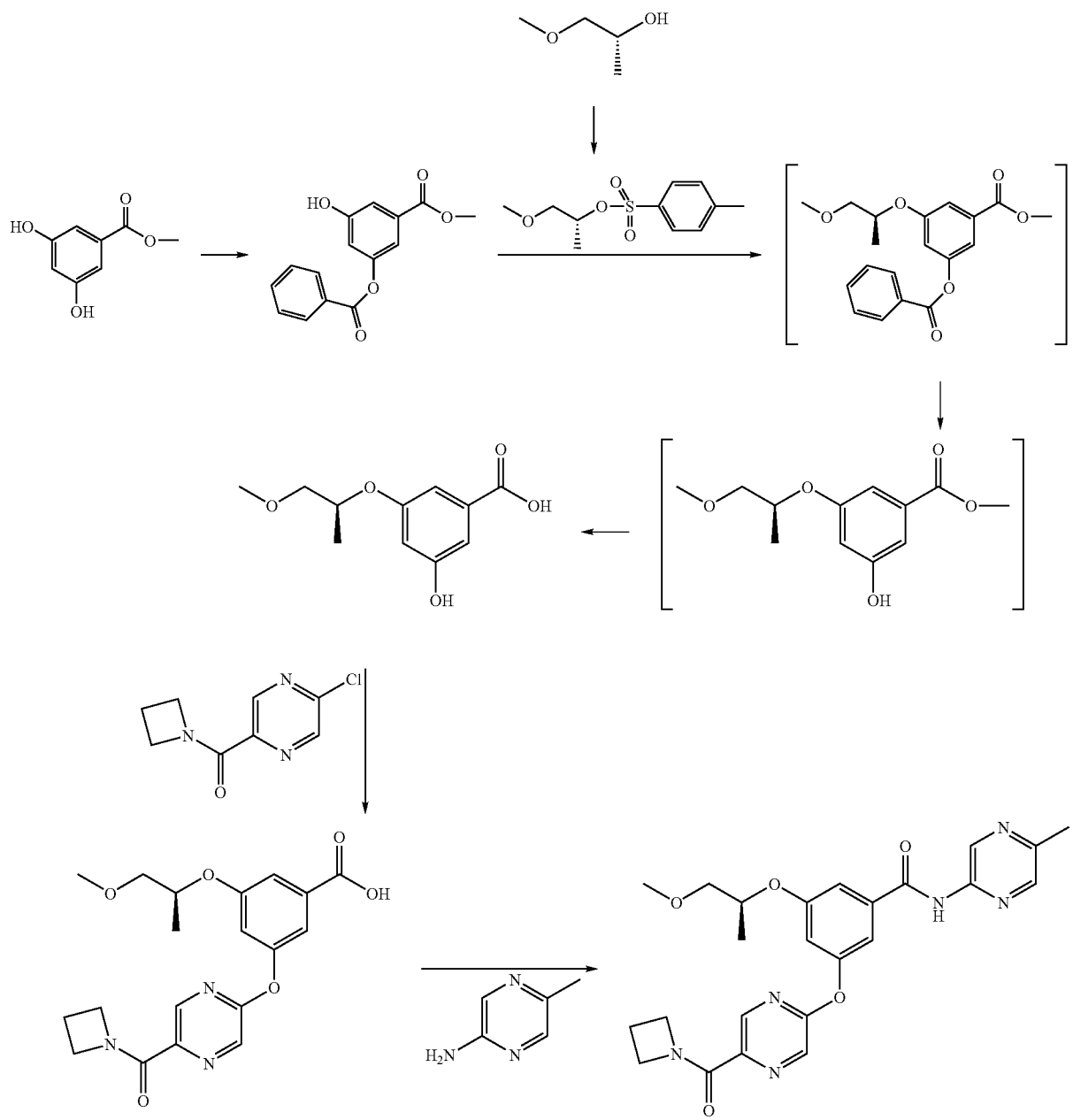

Scheme 2

The invention will now be particularly described by way of the following examples in which the following abbreviations may be used:

vols volume equivalents
eq equivalents
w/w weight for weight
v/v volume for volume
DMSO dimethylsulfoxide
Ts tosylate (p-methylbenzenesulfonate)
TLC thin layer chromatography
NMR nuclear magnetic resonance spectroscopy
MTBE methyl tert-butyl ether In the following non-limiting Examples, unless otherwise stated:
(i) operations were carried out at room temperature, that is in the range 18-25° C. and under an atmosphere of an inert gas such as argon or nitrogen;
(ii) yields are given for illustration only and are not necessarily the maximum attainable;
(iii) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; sextet
(iv) purity of intermediates was assessed by NMR analysis;

Example 1

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide

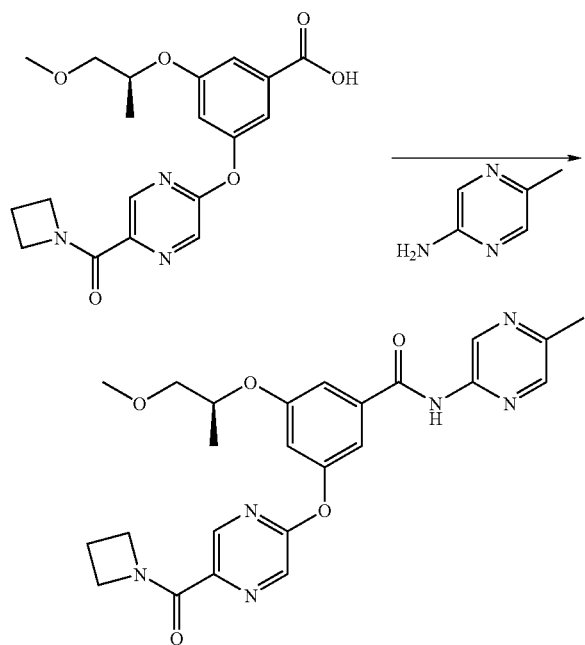

To a flask was added 3-{[5-(azetidin-1-ylcarbonyl)pyrazin-2-yl]oxy}-5-[(1S)-2-methoxy-1-methylethoxy]benzoic acid (1.0 eq), 5-methylpyrazin-2-amine (1.0 eq) and 2-methyltetrahydrofuran (3.5 vols) under a nitrogen atmosphere. The mixture was cooled to 0° C. N-methylmorpholine (5.0 eq) was added at 0° C., then 1-propanephosphonic acid cyclic anhydride (T3P) (supplied as 50% w/w in ethyl acetate) (2.5 eq) was added in one portion via addition funnel over 45 minutes maintaining the reaction temperature at 0-5° C. The addition funnel was washed with 2-methyltetrahydrofuran (0.5 vols), then the reaction mixture was boiled under reflux under nitrogen for at least 14 hours, before being cooled to 22° C. Water (4.0 vols) was added to the reaction mixture in one portion, followed by 2-methyltetrahydrofuran (4.0 vols). After agitating for 30 minutes, the layers were separated. The upper organic layer was retained and the aqueous layer returned to the flask. 2-Methyltetrahydrofuran (4.0 vols) was added to the flask, the mixture was agitated for 30 minutes, then the layers were separated. The organic layers were combined in the flask and further 2-methyltetrahydrofuran (6.0 vols) was then added. The mixture was agitated, and 1.0N hydrochloric acid (4.0 vols) was then added. The mixture was agitated for at least 30 minutes at 22±5° C., and the layers were then separated. 1.0N Hydrochloric acid (4.0 vols) was added to the organic layer. The mixture was agitated for at least 30 minutes at 22±5° C. the mixture was separated 5% w/w Sodium hydrogen carbonate (4.0 vols) solution was added the organic layer. The mixture was agitated for at least 30 minutes at 22±5° C. then the mixture was separated. This process was repeated. Water (4.0 vols) was added to the organic layer, the mixture was agitated for at least 30 minutes at 22±5° C. then the layers were separated. The organic layer was distilled under vacuum at 35° C. collecting 19 vols of distillates. 2-Methyltetrahydrofuran (4 vols) was added, and the distillation was continued under vacuum at 35° C. collecting 6 vols distillates. Further 2-methyltetrahydrofuran (4 vols) was added and the reaction mixture sampled for water content. Further 2-methyltetrahydrofuran (4 vols) was added, and the reaction mixture was filtered through a CUNO™ filter then distilled until the pot volume was approximately 7 vols, then methyl iso-butylketone (11 vols) was added and the mixture vacuum distilled at 35° C. to a pot volume of approximately 7 vols. Methyl iso-butylketone (11 vols) was added and the mixture vacuum distilled at 35° C. to a pot volume of approximately 6 vols. N-Heptane (0.5 vols) was added to the mixture, and the temperature adjusted to 60° C., the mixture was cooled to 46° C., seeded, then cooled to 22° C. and agitated for at least 12 hours. The mixture was filtered. The solid was washed with a mixture of methyl iso-butylketone (1.5 vols)/heptane (0.16 vols). The solid was washed with heptane (~1.5 vols). The isolated solid was dried at 22° C. under vacuum to afford the title compound as an off white solid. Corrected yield was 62%. ¹H NMR δ (400 MHz DMSO) 11.04 (s, 1H), 9.26 (s, 1H), 8.68 (s, 1H), 8.57 (s, 1H), 8.36 (s, 1H), 7.57 (bs, 1H), 7.47 (bs, 1H), 7.13 (bs, 1H), 4.81-4.77 (m, 1H), 4.58-4.54 (t, 2H), 4.11-4.07 (t, 2H), 3.55-3.47 (m, 2H), 3.3 (s, 3H), 2.48 (s, 3H), 2.34-2.26 (m, 2H), 1.26-1.25 (d, 3H)

Preparation of 3-{[5-(azetidin-1-ylcarbonyl)pyrazin-2-yl]oxy}-5-[(1S)-2-methoxy-1-methylethoxy]benzoic acid

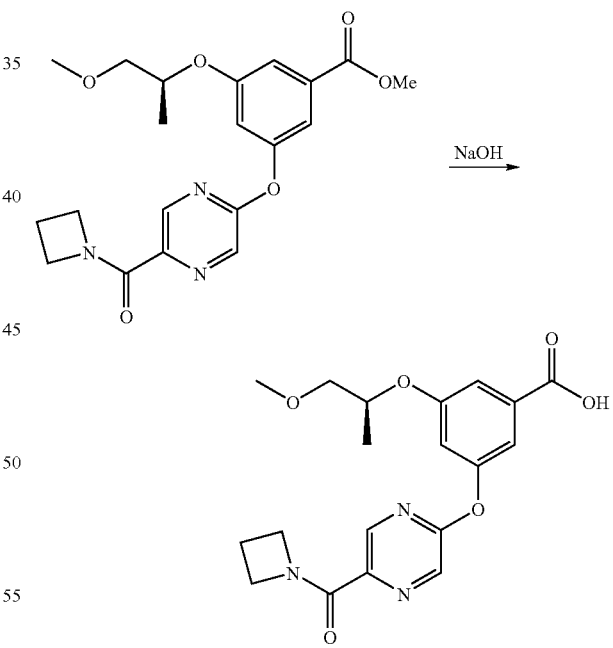

To a flask was added methyl 3-{[5-(azetidin-1-ylcarbonyl)pyrazin-2-yl]oxy}-5-[(1S)-2-methoxy-1-methylethoxy]benzoate (1.0 eq) and N-methylpyrrolidinone (7.6 vols). The contents of the flask were cooled to 10° C. Water (3.9 vols) was added, and the mixture then cooled to approximately −15° C. Sodium hydroxide (1.5 eq) was dissolved in water (2.3 vols), and the sodium hydroxide solution added slowly to the flask over one hour, maintaining the reaction temperature below −10° C. The sodium hydroxide was line washed with water (0.5 vols). The reaction mixture was held for approximately 4 hours. Acetic acid (1.25 eq) was added to the mixture at −10° C. The mixture was allowed to warm to 5° C. Acetic acid (2.37 eq) was added to the mixture, the acetic acid line washed with water (3.5 vols) and the mixture allowed to warm to 22° C. The mixture was seeded, then water (5 vols) was added to the mixture. 2N hydrochloric acid (1.5 eq) was added to the mixture until pH4 was reached. The reaction mixture was stirred for at least 14 hours, then cooled to 10° C., stirred for 1 hour at 10° C. The mixture was filtered. The solid was slurry washed with water (3×2.5 vol). The isolated solid was dried at 25° C. under vacuum to afford the title compound as an off white solid.

The solid was charged to a flask, followed by ethyl acetate (27.2 vols), and the mixture heated to reflux for at least 30 minutes. The mixture was filtered hot and approximately 13 vols removed by vacuum distillation. The mixture was cooled to 15° C., and agitated overnight at this temperature. The mixture was filtered, and the (solid) washed with ethyl acetate (2.25 vols). The isolated solid was dried at 25° C. under vacuum to afford the title compound as an off white solid. The corrected yield was 78%.

$^1$H NMR δ (400 MHz DMSO): 8.66 (s, 1H), 8.55 (s, 1H), 7.36 (s, 1H), 7.31 (s, 1H), 7.16 (s, 1H), 4.71-4.65 (m, 1H), 4.58-4.54 (t, 2H), 4.11-4.07 (t, 2H), 3.52-3.41 (m, 2H), 3.29 (s, 3H), 2.33-2.26 (m, 2H), 1.24-1.2 (d, 3)

Preparation of methyl (3-{[5-azetidinyl-1-ylcarbonyl)pyrazin-2-yl]oxy}-5-{[1S)-1-methyl-2-(methyloxy)ethyl]oxy})benzoate

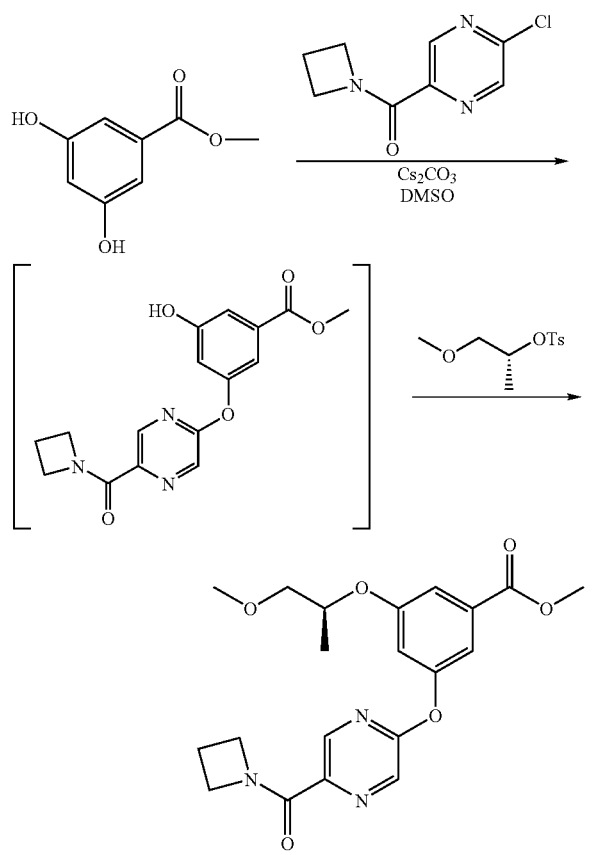

To a clean, dry, suitably serviced flask (flask A) fitted with overhead stirrer, thermometer, condenser, and nitrogen line was added methyl 3,5-dihydroxybenzoate (1.0 eq), 2-(azetidin-1-ylcarbonyl)-5-chloropyrazine (1.0 eq), cesium carbonate (3.5 eq), and dimethylsulfoxide (9.4 vols) under a nitrogen atmosphere. The reaction vessel was heated to 45° C. under a nitrogen atmosphere for at least 14 hours. (1R)-2-Methoxy-1-methylethyl 4-methylbenzenesulfonate (1.3 eq) was added over 45 minutes. The mixture was agitated at 45° C. for at least 14 hours then cooled to 22° C. and iso-propylacetate (10 vols) added. Water (12 vols) was added over 25 minutes at 25° C., and the mixture was agitated for 15 minutes at 22° C. The organic layer was separated off, after which the aqueous layer was re-extracted with (2×5 vols) iso-propylacetate. The iso-propyl acetate layers were combined and water (8 vols) was added. The mixture was agitated at 22° C. for 30 minutes. The aqueous layer was separated off and discarded. This process was repeated. The organic layer was distilled under vacuum to constant weight.

Meanwhile neutral alumina (18 weight eq) was mixed in a flask with iso-propyl acetate (4.5 vols) and heptane (11.2 vols). This mixture was added to a large chromatography column and the reaction mixture compressed on the column. The mobile organic layer was diluted with iso-propyl acetate (0.2 vols) and heptane (0.4 vols). The mobile organic layer was then added to the column and eluted sequentially with 1:4 v/v iso-propyl acetate/heptane (50 vols), 1:3 v/v iso-propyl acetate/heptane (20 vols) and 6:4 v/v iso-propyl acetate/heptane (100 vols). Fractions were analysed by TLC, and fractions that contained clean product evaporated on the rotary evaporator to give the title compound as a thick oil in 59% corrected yield. $^1$H NMR (400 MHz, DMSO): δ 8.62 (s, 1H), 8.50 (s, 1H), 7.34 (s, 1H), 7.30 (s, 1H), 7.17 (s, 1H), 4.68-4.64 (m, 1H), 4.54-4.50 (t, 2H), 4.07-4.03 (t, 2H), 3.81 (s, 3H), 3.49-3.41 (m, 2H), 3.25 (s, 3H), 2.29-2.21 (m, 2H), 1.20-1.18 (d, 3H)

Preparation of (1R)-2-methoxy-1-methylethyl 4-methylbenzenesulfonate

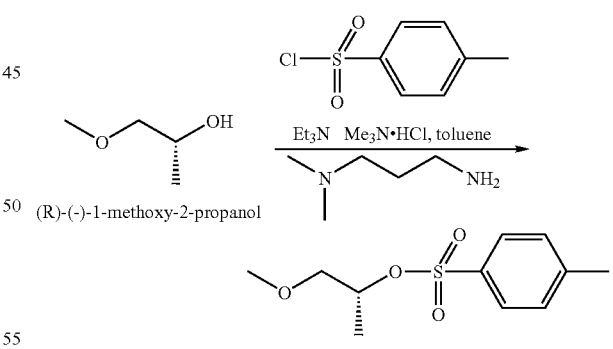

To a flask was added under a nitrogen atmosphere trimethylamine hydrochloride (0.1 eq), tosyl chloride (1.3 eq) and toluene (5 vols) and the reaction mixture agitated to form an oily slurry. The slurry was cooled to −5° C. (2R)-1-Methoxypropan-2-ol (1.0 eq) was added drop-wise over 30 minutes. Toluene (2.5 vols) was added as a wash followed by triethylamine (1.5 eq), which was added drop-wise via addition funnel over 30 minutes maintaining the reaction temperature <8° C. Further toluene (2.5 vols) was added as a wash and the reaction mixture held at −5° C. to 5° C. for 4.5 hours. N,N-Dimethyl-1,3-propane-diamine (0.3 eq) was added over 10 minutes at −5° C. The mixture was agitated at −5° C. to 5° C. for 30 minutes. Then 2N hydrochloric acid (0.55 eq) and 70 ml water were added. The mixture was agitated for 30 minutes at 22° C. and the aqueous layer was separated off and discarded. The mixture was washed twice more with water (10 vols each wash) and after separation of the aqueous wash, the toluene layer was distilled to an oil on the rotary evaporator. Toluene (20 vols) was added to the oil and the solution evaporated to give the title compound as a dry light brown oil. Yield (corrected for assay) 93-97%. $^1$H NMR (400 MHz CDCl$_3$): δ 7.78-7.75 (d, 2H), 7.45-7.43 (d, 2H), 4.66-4.62 (m, 1H), 3.35-3.26 (m, 2H), 3.16 (s, 3H), 2.4 (s, 3H), 1.13-1.11 (d, 3H)

Preparation of methyl
3-hydroxy-5-[(phenylcarbonyl)oxy]benzoate

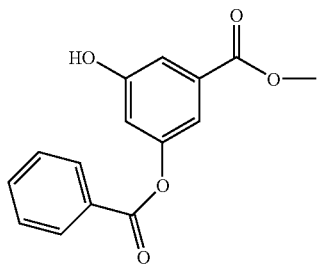

To a flask fitted with thermometer, condenser, overhead stirrer, pH probe and nitrogen line was added methyl-3,5-dihydroxybenzoate (1.0 eq), sodium phosphate mono-basic monohydrate (0.46 eq) and water (10.5 vols) under a nitrogen atmosphere. The temperature was adjusted to 20° C.±3° C. 10% w/w Sodium hydroxide was added to adjust the pH to pH 7.8±0.2. Benzoyl chloride (1.0 eq) was added drop-wise in small portions over 1-2 hours, and sodium hydroxide was added concurrently drop-wise in small portions over the same time period to maintain the reaction in a pH range of pH 7.8±0.2 and at a reaction temperature of 20° C.±3° C. The crude reaction mixture was agitated for a further 30 minutes, filtered, and then washed with 4 vols of a solution prepared from water (4 vols), sodium phosphate mono-basic monohydrate (0.05 eq), and adjusted to pH7.5 with 10% w/w sodium hydroxide. The crude solid was then washed with 4 vols of a solution prepared from water (4 vols), sodium phosphate mono-basic monohydrate (0.05 eq), and adjusted to pH6.5 with 10% w/w sodium hydroxide. The crude solid was then dissolved in iso-propyl acetate (8 vols) and water (2 vols) and the mixture agitated for at least 30 minutes to ensure the solid had dissolved. The mixture was filtered through a CUNO™ filter to remove a small amount of brown solid. The aqueous layer was separated off. Water (2 vols) was added to the organic layer and the batch agitated for at least 30 minutes. The aqueous layer was separated off and the organic layer was vacuum distilled, keeping the batch temperature below 40° C. to reduce the volume to 5-6 vols. Toluene was added then added (5 vols) and the mixture was vacuum distilled keeping the batch temperature below 40° C., reducing the volume to approximately 3.5 vols. The mixture was cooled to 15° C.±3° C. and agitated at this temperature for at least 30 minutes, then filtered, and the solid washed with toluene (1 vol). The product was dried at 20° C.-40° C. to give the desired product as a solid (corrected yield 40%-70%).

$^1$H NMR δ (400 MHz; CDCl$_3$): 8.21-8.18 (d, 2H), 7.67-7.63 (t, 1H), 7.54-7.49 (t, 2H), 7.44 (d, 2H), 6.98-6.96 (t, 1H), 6.7 (bs, 1H), 3.90 (s, 3H).

Alternatively methyl 3-hydroxy-5-[(phenylcarbonyl)oxy] benzoate may be made by the following process:

To a flask fitted with thermometer, condenser, overhead stirrer, pH probe and nitrogen line was added methyl-3,5-dihydroxybenzoate (1.0 eq), 325 mesh potassium carbonate (3.0 eq) and dimethylformamide (DMF) (4 vols) under a nitrogen atmosphere. The mixture was heated to 47° C. for 1 hour, then benzoyl chloride (1.0 eq) was added slowly drop-wise via syringe pump over approximately 2 hours. Further benzoyl chloride was added (0.1 eq) over 20 minutes via syringe pump. The reaction mixture was held for 1.5 hours, then water (10 vols) and iso-propyl acetate (6 vols) were added. The reaction mixture was agitated for 30 minutes and then the layers were separated. The aqueous layer was re-extracted with a further charge of iso-propyl acetate (6 vols). The batch was separated, and the combined organic layers were washed with saturated brine (6 vols), then with a solution of 0.1N hydrochloric acid/brine. The iso-propyl acetate was distilled to dryness on the rotary evaporator. Iso-propyl acetate (6 vols) was added, and distilled to dryness on the rotary evaporator. Toluene (6 vols) was added and distilled to dryness on the rotary evaporator. Toluene (3.5 vols) was added and the reaction slurried for 30 minutes. The solid was filtered off and dried at 20° C.-40° C. to give the desired product as a solid (corrected yield 72%).

Alternative Preparation of methyl
3-hydroxy-5-[(phenylcarbonyl)oxy]benzoate

To an inerted flask fitted with thermometer, condenser, overhead stirrer, pH probe and nitrogen line was charged methyl 3,5-dihydroxy benzoate and suspended in 10 vol water. The pH of the suspension was adjusted to 8.0 using an aqueous solution of 2.5% w/w lithium hydroxide and 2.5% w/w potassium carbonate. A solution of benzoyl chloride (1.0 eq.) in 2 vol toluene was added at such a rate that the internal temperature could be maintained between 20 and 22° C. The pH of the solution was maintained between 7.9 and 8.1 by simultaneous addition of an aqueous solution of 2.5% lithium hydroxide and 2.5% potassium carbonate (approximately 5 vol). The resulting suspension was agitated for further 60 minutes at 20-22° C. and then filtered. The filter cake was washed twice with water (2 vol each) and pulled dry. The crude product obtained was then dissolved in isopropyl acetate (8 vol) before Diatomaceous earth was added and the slurry was stirred for 1 h. Following filtration of the suspension the product is then solvent-swapped from isopropyl acetate into toluene (5 vol) by vacuum distillation maintaining the internal temperature at or below 45° C. The resulting suspension was cooled to 15° C., agitated for 1 h and then filtered. After washing the filter cake with 1 vol toluene the product was dried to constant weight yielding typically 75-80% of the title product at >98% purity.

Preparation of (1R)-2-methoxy-1-methylethyl 4-methylbenzenesulfonate

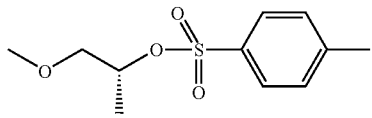

To a flask fitted with overhead stirrer, condenser, thermometer and nitrogen line was added trimethylamine hydrochloride (0.1 eq), tosyl chloride (1.3 eq) and toluene (5 vols) under a nitrogen atmosphere and the reaction mixture agitated to form an oily slurry. The slurry was cooled to −5° C., then (2R)-1-methoxypropan-2-ol (1.0 eq) was added drop-wise over 30 minutes. Toluene (2.5 vols) was added as a line wash followed by triethylamine (1.5 eq), which was added dropwise via addition funnel over 30 minutes maintaining the reaction temperature <8° C. Further toluene (2.5 vols) was added as a line wash and the reaction mixture held at −5° C. to 5° C. for 4.5 hours. N,N-dimethyl-1,3-propane-diamine, (0.3 eq) was added over 10 minutes at −5° C. The reaction mixture was agitated at −5° C. to 5° C. for 30 minutes, then 2N hydrochloric acid (0.55 eq) and 70 ml water were added. The reaction mixture was agitated for 30 minutes at 22° C. and the aqueous layer was separated off and discarded. The mixture was washed twice more with water (10 vols each wash) then the toluene layer was distilled to an oil on the rotary evaporator. Toluene (20 vols) was added to the oil and the solution evaporated to an oil to give the title compound as a dry light brown oil. Yield corrected for assay 93-97%. ¹H NMR δ (400 MHz CDCl₃): 7.78-7.75 (d, 2H), 7.45-7.43 (d, 2H), 4.66-4.62 (m, 1H), 3.35-3.26 (m, 2H), 3.16 (s, 3H), 2.4 (s, 3H), 1.13-1.11 (d, 3H).

Preparation of (1R)-2-methoxy-1-methylethyl 4-(trifluoromethyl)benzenesulfonate)

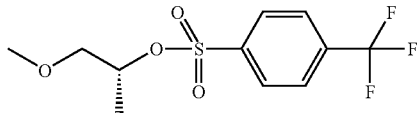

To a flask was added 4-trifluoromethylsulfonylchloride (1.3 eq) and toluene (10 vols), the reaction mixture was cooled to 5° C., then (2R)-1-methoxypropan-2-ol (1.0 eq) was added at 5° C. Trimethylamine hydrochloride (0.1 eq) was added at 5° C., then triethylamine (1.5 eq) added slowly drop-wise over 50 minutes maintaining the reaction temperature between 5-12° C. After holding for approximately 18 hours at 5° C., the reaction was quenched by the dropwise addition of 3-dimethylaminopropane (0.3 eq) over minutes at 5° C. The reaction mixture was stirred for 2 hours at 5° C., then water (5 vols) added at 5° C., then 5N hydrochloric acid (2 vols) was added slowly at 5° C. The reaction mixture was warmed to 20° C., water (1 vol) was added followed by toluene (10 vols). The reaction mixture was warmed to 30° C., then the aqueous layer separated off and discarded. Water (5 vols) was added and the reaction mixture agitated for 30 minutes, then the water layer separated off and discarded. 8% w/w Sodium carbonate (4 vols) was added, the reaction mixture agitated for 30 minutes, then the water layer separated off and discarded. Water (5 vols) was added, the batch agitated for 30 minutes, then the water layer separated off and discarded. This water wash was repeated twice. The organic layer was evaporated to an oil on the rotary evaporator. Toluene was added and the organic layer was evaporated to an oil on the rotary evaporator. This process was repeated to give the desired product as a yellow oil (corrected yield 97%). ¹H NMR δ (400 MHz CDCl₃) 8.07-8.05 (d, 2H), 7.82-7.80 (d, 2H), 4.84-4.80 (m, 1H), 3.44-3.35 (m, 1H), 3.19 (s, 3H), 1.35-1.33 (d, 3H)

Preparation of 3-hydroxy-5-[(1S)-2-methoxy-1-methylethoxy]benzoic acid

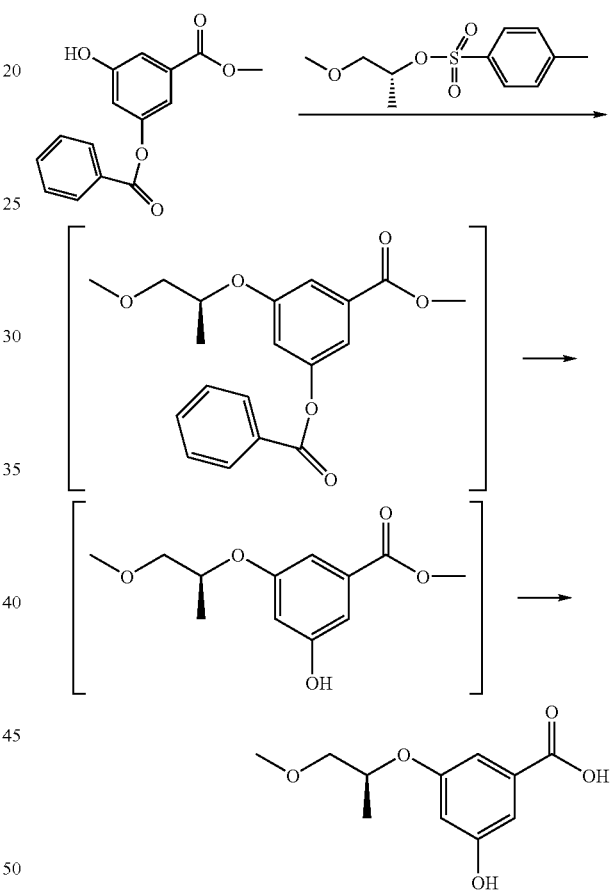

To a flask fitted with overhead stirrer, condenser, thermometer and nitrogen line was added methyl 3-hydroxy-5-[(phenylcarbonyl)oxy]benzoate (1.0 eq), cesium carbonate (1.5 eq) and dimethylsulfoxide (7.0 vols) under a nitrogen atmosphere. The batch was heated to 40-45° C. (1R)-2-methoxy-1-methylethyl 4-methylbenzenesulfonate (1.3 eq) was added slowly dropwise over at least 90 minutes maintaining reaction temperature at 40-45° C. The reaction mixture was held for at least 8 hours and then was cooled to 15±4° C. Iso-propyl acetate (4.0 vols) was added followed by water (5.0 vols), keeping the reaction temperature below 25° C. The reaction mixture was agitated for approximately 15 minutes and then the layers were separated. The organic phase was retained. The aqueous phase was re-extracted with further iso-propyl acetate (3 vols). The reaction mixture was agitated for approximately 15 minutes and then the layers separated. This process was repeated with further isopropyl acetate and the organic phases were combined and then washed with water (3 vols). After approximately 15 minutes agitation the layers were separated, and water (3 vols) was added to the organic layer. After approximately 15 minutes agitation the layers were separated and the organic layer was vacuum distilled at 40° C. until no more solvent could be distilled. Methanol (7 vols) was added, then sulphuric acid (0.8 eq) was added and the mixture was heated to reflux for at least 16±4 hours. The reaction mixture was vacuum distilled at 40° C. until a pot volume of 2.5-3 vols was achieved. Toluene (4 vols) was added to the flask, and vacuum distillation continued at 35° C. until a pot volume of 4.0 vols was achieved. The mixture was cooled to 20±5° C. Water (15 vols) was added to the reaction mixture and the mixture agitated at 20±5° C. for at least 15 minutes. The batch was separated and the organic layer was cooled to 0-5° C., before 0.5M sodium hydroxide (1.0 eq) was added slowly keeping the batch temperature below 5° C. The vessel was agitated for 15 minutes and then separated. The aqueous layer was retained and the organic layer was treated with 0.5M sodium hydroxide (1.0 eq; added slowly keeping the batch temperature below 5° C.). The vessel was agitated for 15 minutes and then the layers were separated. The aqueous layers were combined and toluene (3 vols) added slowly keeping the batch temperature below 5° C. The vessel was agitated for 15 minutes and then separated. The aqueous layer was warmed to 25±5° C., and 33% w/w sodium hydroxide added (0.5 eq). After 2 hours stirring, 37% w/w hydrochloric acid (2.1 eq) was added to adjust the pH to pH ≦2. Methyl tert-butyl ether (3 vols) was added, the mixture was agitated for 15 minutes, then the layers separated. The organic layer was retained. The aqueous layer was re-extracted with MTBE (3 vols) and the combined organic layers were distilled under vacuum at 35° C. to a pot volume of approximately 3 vols, collecting 3 vols distillates. Toluene (5 vols) was added, and the batch temperature adjusted to 50° C. Water (1 vol) was added and the batch agitated for at least 15 minutes at this temperature then the layers were separated. The organic layer filtered through a filter then distilled at 35° C. until the mixture became turbid. The material was cooled to 20° C., seeded with 3-hydroxy-5-[(1S)-2-methoxy-1-methylethoxy]benzoic acid and agitated at this temperature for 3 hours. The mixture was then distilled under vacuum at 25° C. removing further MTBE, and then cooled to 5° C. for at least 2 hours. The mixture was filtered, and the solid was washed with toluene (1 vol) at 20° C. The batch was dried with vacuum or under a stream of nitrogen until constant weight was attained at 20° C. After drying, the title compound was obtained as a solid (corrected yield typically 40-50%). $^1$H NMR δ (400 MHz DMSO): 12.82 (bs, 1H), 9.74 (bs, 1H), 6.95 (bs, 1H), 6.91 (bs, 1H), 6.56-6.55 (t, 1H), 4.59-4.52 (m, 1H), 3.5-3.41 (m, 2H), 3.28 (s, 3H), 1.21-1.19 (d, 3H).

Alternative Preparation of 3-hydroxy-5-[(1S)-2-methoxy-1-methylethoxy]benzoic acid Methyl 3-hydroxy-5-[(phenylcarbonyl)oxy]benzoate (1.0 eq.), (R)-1-methoxy-2-propanol (1.25 eq.) and triphenylphosphine (1.25 eq.) were suspended in toluene (10 vol). Diisopropyl azodicarboxylate (1.25 eq.) was added at a batch temperature of between 0 and 5° C. over ~2 h. The mixture was allowed to warm to room temperature and was stirred for further 30 min at this temperature. The resulting suspension was filtered to remove the bulk of the triphenylphosphine oxide formed and the filter cake was washed with toluene (1.5 vol). To the combined toluene fractions containing the resulting methyl 3-[(1S)-2-methoxy-1-methylethoxy]-5-[(phenylcarbonyl)oxy]benzoate was added sodium methylate (0.8 eq.) at a batch temperature of between 20 and 30° C. and the mixture was stirred to 1 h. The solution of the resulting methyl 3-hydroxy-5-[(1S)-2-methoxy-1-methylethoxy]-benzoate was then extracted twice with KOH 0.25 M (3.5 vol each) at a batch temperature of between 0 and 5° C. KOH was then added (1 eq.) to hydrolyse the ester moiety and the batch was stirred for 1 h at a temperature of between 20 and 30° C. The pH of the aqueous phase is then adjusted to 1.5 using conc. hydrochloric at a batch temperature of <30° C. Crude 3-hydroxy-5-[(1S)-2-methoxy-1-methylethoxy]benzoic acid was subsequently extracted into MTBE (2×3 vol) before activated charcoal was added. The batch was stirred for 10 minutes and then filtered. The batch was reduced to 3 pot volumes by distillation at a batch temperature of <45° C. Toluene (4 vol) and heptane (1 vol) were added and vacuum distillation was continued at a batch temperature of <50° C. until no further MTBE was collected. The batch was cooled to a temperature of <40° C., seeded and further cooled to a batch temperature of between 28 and 32° C. The resulting suspension was stirred for 1 h at this temperature before being further cooled to 5 to 10° C. After 2 h stirring at 5 to 10° C. the batch was filtered and washed with cold toluene (1 vol.). Drying at <60° C. furnished 3-hydroxy-5-[(1S)-2-methoxy-1-methylethoxy] benzoic acid in >99% purity as colourless solid with a melting point of 95° C. in a typical yield between 65 and 70% from methyl 3-hydroxy-5-[(phenylcarbonyl)oxy]benzoate.

Methyl 3-[(1S)-2-methoxy-1-methylethoxy]-5-[(phenylcarbonyl)oxy]benzoate $^1$H NMR (400 MHz, CDCl$_3$) δ 8.21-8.17 (d, 2H), 7.66-7.62 (t, 1H), 7.54-7.49 (m, 4H), 7.03-7.02 (t, 1H), 4.64-4.60 (m, 1H), 3.9 (s, 3H), 3.61-3.49 (m, 2H), 3.45 (s, 3H), 1.35-1.33 (d, 3H)

$^{13}$C NMR data (100.55 MHz, CDCl$_3$) δ 166.2, 164.91, 158.88, 151.79, 133.87, 132.25, 130.28, 129.28, 128.71, 115.6, 114.95, 114.27, 75.7, 73.83, 59.45, 52.44, 16.72.

Methyl 3-hydroxy-5-[(1S)-2-methoxy-1-methylethoxy]benzoate $^1$H NMR (400 MHz, DMSO) δ 6.93 (s, 1H), 6.90 (s, 1H), 6.57 (bs, 1H), 4.55-4.51 (m, 1H), 3.79 (s, 3H), 3.47-3.41 (m, 2H), 3.26 (s, 3H), 1.18-1.17 (d, 3H)

Preparation of 3-hydroxy-5-[(1S)-2-methoxy-1-methylethoxy]benzoic acid (t-butylamine salt)

To a flask fitted with overhead stiffer was added 3-hydroxy-5-[(1S)-2-methoxy-1-methylethoxy]benzoic acid (1.0 eq) and acetonitrile (6 vols). Tert-butylamine (1.0 eq) was added at 22° C., followed by acetonitrile (3 vols). After stirring for at least 5 hours, the reaction mixture was filtered and dried in a vacuum oven to give the title compound as a crystalline white solid (73.6%). $^1$H NMR (400 MHz DMSO) δ: 6.90 (bs, 1H), 6.85 (s, 1H), 6.30-6.29 (t, 1H), 4.47-4.43 (m, 1H), 3.47-3.35 (m, 2H), 3.09 (s, 3H), 1.22 (s, 9H), 1.17-1.16 (d, 3H). Melting point by Differential Scanning Calorimetry (DSC) 154.7° C.

Preparation of 3-hydroxy-5-[(1S)-2-methoxy-1-methylethoxy]benzoic acid (potassium salt)

KOH liquor (1.04 eq. of 50.4 wt %) was added to a stirred, nitrogen sparged solution of 3-hydroxy-5-[(1S)-2-methoxy-1-methylethoxy]benzoic acid (1 eq.) in undried 1-propanol (4.87 vol.). At the end of the addition, water (0.33 vol.) and toluene (3.43 vol.) were separately added to the resulting slurry. The jacket temperature was raised to 67° C. before being subjected to the following cooling profile: 67° C. to 64° C. over 3 h, 64 to 57° C. over 3 h, 57 to 45° C. over 3 h, and 45 to 20° C. over 3 h. 6 h after the end of this ramp, the jacket temperature was lowered to 0° C. over 3 h, the jacket was foil wrapped and desupersaturation was allowed to complete overnight (>6 h). The slurry was isolated by filtration through an 11 micron filter paper. The cake was sequentially washed twice with an equal weight of an ice-cold solution of toluene (41.79 wt %) in 1-propanol. The cake was dried in a 40° C. house vacuum oven to give 3-hydroxy-5-[(1S)-2-methoxy-1-methylethoxy]benzoic acid potassium salt as tri-hydrate in a typical yield of 93% of theoretical yield.

$^1$H NMR (400 MHz, $d_6$-DMSO) 9.05 (1H, br s), 6.86-6.83 (2H, m), 6.18 (1H, dd, J=2.3, 2.3), 4.44 (1H, qdd, 6.2, 5.1, 5.1), 3.48-3.33 (8H, m), 3.28 (3H, s), 1.18 (3H, d, J=2.3)

Other salts of 3-hydroxy-5-[(1S)-2-methoxy-1-methylethoxy]benzoic acid, e.g. sodium, calcium or magnesium salts, were formed in a similar way using appropriate bases, e.g. sodium hydroxide, magnesium hydroxide or calcium hydroxide or by salt exchange for example by using potassium acetate or potassium 2-ethyl hexanoate (in propan-2-ol) for the potassium salt or using calcium bis-(2-ethylhexanoate) for the calcium salt.

Process for Enzymatic Conversion of (methyl 3-[(1S)-2-methoxy-1-methylethoxy]-5-[(phenylcarbonyl)oxy]benzoate to methyl 3-hydroxy-5-[(1S)-2-methoxy-1-methylethoxy]benzoate To a flask fitted with thermometer and magnetic stirrer was added (methyl 3-[(1S)-2-methoxy-1-methylethoxy]-5-[(phenylcarbonyl)oxy]benzoate) (1.0 eq), and tert-butanol (90 vols) followed by addition of either water (10 vols) or pH7 buffer (10 vols). Enzyme 1 wt eq (either AE 01 Lipase Cl or Alphamerix AE-02) was added and the reaction agitated at 36° C. for several days (such as 7 days) until the reaction was complete.

Preparation of 3-{[5-(azetidin-1-ylcarbonyl)pyrazin-2-yl]oxy}-5-[(1S)-2-methoxy-1-methylethoxy]benzoic acid

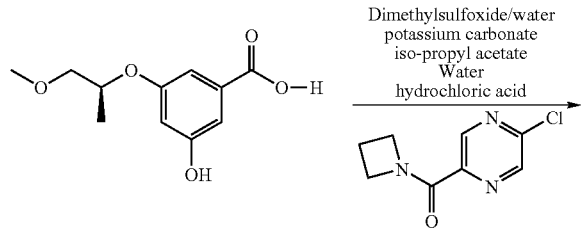

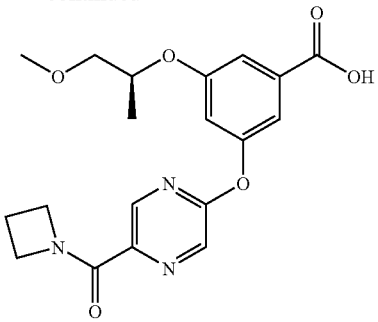

To a clean dry flask fitted with thermometer, condenser, overhead stirrer and nitrogen line was added 3-hydroxy-5-[(1S)-2-methoxy-1-methylethoxy]benzoic acid* (1.0 eq), potassium carbonate (2.5 eq), dimethylsulfoxide (3 vols) and water (1.0 vols) under a nitrogen atmosphere. The resulting mixture was heated to 45° C.-55° C. for at least one hour. 2-(Azetidin-1-ylcarbonyl)-5-chloropyrazine (1.05 eq) was dissolved in dimethylsulfoxide (5.0 vols) at about 40° C.-50° C. The solution of 2-(azetidin-1-ylcarbonyl)-5-chloropyrazine in DMSO was added drop-wise via syringe pump to the above reaction mixture over 1-4 hours maintaining the reaction temperature at 45° C.-55° C. The reaction was stirred for 16 hours at 45° C.-55° C. The bath was cooled to 22±3° C. Water (8 vols) was added, followed by iso-propyl acetate (10 vols). The contents were agitated at 22° C. for 15 minutes then the layers were separated The aqueous layers was treated with iso-propylacetate (10 vols) and the mixture agitated at 22±3° C. for at least 15 minutes. The layers were separated and the aqueous layer was treated again with iso-propylacetate in the same manner. The layers were separated, the organic layer was discarded and 5N hydrochloric acid (~4.4 eq) was added drop-wise over at least 30 minutes to the aqueous layer to a pH end-point of pH 3-0-pH4.0 whilst maintaining the reaction temperature at 22±3° C. Iso-propylacetate (10 vols) was then added and the mixture heated to 75° C. The mixture was agitated at this temperature for at least 30 minutes, then the temperature was adjusted to 70° C. and the layers were separated. The organic layer was retained, and the aqueous layer treated with iso-propylacetate (10 vols) and the mixture heated to 75° C. The mixture was agitated at this temperature for at least 30 minutes, then the temperature was adjusted to 70° C. and the layers separated. The organic layer was retained, and the aqueous layer discarded. The combined organic layers from the previous 2 separations were reheated to reflux for dissolution. Water (5 vols) was added and the mixture stirred at 70-75° C. for at least 15 minutes. The batch temperature was adjusted to 70° C. and the aqueous layer separated off and discarded. This process was repeated twice with a further 5 vols of water at each time. The organic layer was set to distil at atmospheric pressure to a pot volume of 4 vols. Iso-propyl acetate (8 vols) was added and the batch set to distil to a pot volume of approximately 4 vols. The batch was cooled to 22° C. over 2 hours, the batch was agitated at 22° C. for 3 hours, then cooled to 0° C., the mixture was held at 0° C. for 5 hours, then filtered, and the solid washed with iso-propylacetate (20 ml, 4 vols). After drying in the vacuum oven at 50° C. overnight, the desired product was obtained as a solid (corrected yield 85-90%). $^1$H NMR δ (400 MHz DMSO): 8.66 (s, 1H), 8.55 (s, 1H), 7.36 (s, 1H), 7.31 (s, 1H), 7.16 (s, 1H), 4.71-4.65 (m, 1H), 4.58-4.54 (t, 2H), 4.11-4.07 (t, 2H), 3.52-3.41 (m, 2H), 3.29 (s, 3H), 2.33-2.26 (m, 2H), 1.24-1.19 (d, 3H)

*Alternatively, salts of this acid may be used in this procedure, either directly or after transformation into the free acid by cracking the salt by appropriate method, eg: acidification and extraction, adding NaOH then distilling, or any other process known in the art.

Preparation of 3-{[5-(azetidin-1-ylcarbonyl)pyrazin-2-yl]oxy}-5-[(1S)-2-methoxy-1-methylethoxy]benzoic acid Alternative Method
3-Hydroxy-5-[(1S)-2-methoxy-1-methylethoxy]benzoic acid (5.00 g, 22.10 mmol) and tetra n-butyl phosphonium chloride (6.53 g, 22.1 mmol) were suspended in 2-methyltetrahydrofuran (25 ml, 5 vol rel. to the benzoic acid) and 22 mL water at ambient temperature under nitrogen. Solid potassium carbonate (27.98 g, 202.4 mmol) was charged portionwise with vigorous mechanical stirring. At the end of addition KOH liquor (2.46 g 50% wt/wt in water, 22.1 mmol) was added before the biphasic slurry was heated to 50° C. Once the temperature had stabilised, 2-(azetidin-1-ylcarbonyl)-5-chloropyrazine (4.586 g, 23.21 mmol) was charged portionwise over 40 minutes and the mixtures was stirred over night under nitrogen at 50° C. The phases were split and the lower aqueous phase was run off 25 ml of toluene and 50 mL water were added to the remaining dark red organic phase. The pH of the aqueous phase was then adjusted to 7.0 using conc. hydrochloric acid. The jacket temperature was adjusted to 20° C. and the phases were separated again (the lower aqueous phase was run off and retained; the upper organic phase was discarded). The aqueous phase was washed with more toluene (25 mL). After phase separation the toluene phase was removed again. The pH of the retained aqueous phase was adjusted to 2.1 using 5M hydrochloric acid solution (7.1 mL). Isopropyl acetate (34.9 g) was charged and the jacket temperature was raised to 80° C. Equilibration was performed with the jacket temperature set to 80° C. After phase split the lower aqueous phase was run off again and back-extracted with more isopropyl acetate (17.4 g). The organic phases were combined and homogenised at 80° C. before being washed with water (10 mL). The organic phase was dried by azeotropic distillation under slight vacuum at constant batch volume (batch partially crystallised). The suspension was cooled to 0° C. over 13.5 h and the batch was isolated by filtration followed by a cake-wash with isopropyl acetate (17.4 g). After drying at 40° C. in a vacuum oven overnight 5.25 g at 96% strength (59% corrected yield) of the desired product was obtained as white solid.

3-{[5-(Azetidin-1-ylcarbonyl)pyrazin-2-yl]oxy}-5-[(1S)-2-methoxy-1-methylethoxy]-N-(5-methylpyrazin-2-yl)benzamide

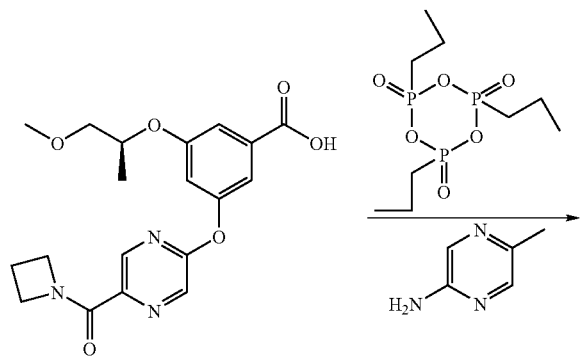

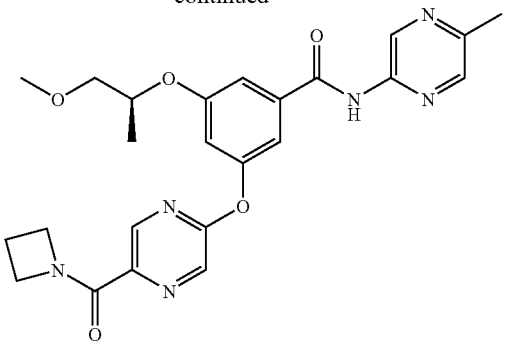

To a flask fitted with overhead stirrer, thermometer, condenser, and nitrogen line was added 3-{[5-(azetidin-1-ylcarbonyl)pyrazin-2-yl]oxy}-5-[(1S)-2-methoxy-1-methylethoxy]benzoic acid (1.0 eq), 5-methylpyrazin-2-amine (1.12 eq) and 2-methyltetrahydrofuran (4.4 vols) under a nitrogen atmosphere. The mixture was cooled to 5° C., and then N-methylmorpholine (5.0 eq) added drop-wise over at least 15 minutes maintaining the temperature at 5±5° C. 1-Propanephosphonic acid cyclic anhydride (T3P) (as 50% w/w solution in ethyl acetate) (2.5 eq) was added drop-wise over at least 15 minutes maintaining the temperature at 5±5° C. The mixture was heated to reflux for at least 16 hours then cooled to 22±5° C. Water (4.0 vols) was added to the reaction mixture, followed by 2-methyltetrahydrofuran (4.0 vols). After agitating for 30 minutes, the mixture was separated. The upper organic layer was retained and the aqueous layer treated with 2-methyltetrahydrofuran (4.0 vols). After agitating for 30 minutes, this mixture was separated. The organic layers were combined and further 2-methyltetrahydrofuran (6.0 vols) was then added. The mixture was agitated, and 1.0N hydrochloric acid (4.0 vols) was added. The mixture was agitated for at least 30 minutes at 22±5° C., and the layers were then separated. The organic layer was treated with 1.0N hydrochloric acid (4.0 vols) then the mixture was agitated for at least 30 minutes at 22±5° C., then the layers were separated. The organic layer was treated with 5% w/w sodium hydrogen carbonate (4.0 vols). The mixture was agitated for at least 30 minutes at 22±5° C., the layers were separated. The organic layer was treated again with 5% w/w sodium hydrogen carbonate (4.0 vols) following the same procedure, and then with water (4.0 vols) following the same procedure. The organic layer was then distilled at atmospheric pressure to a pot volume of 4.7 vols. Methyl iso-butylketone (10 vols) was added, and the batch distilled at atmospheric pressure to a pot volume of 4.68 vols. Methyl iso-butylketone (10 vols) was added, and the batch distilled at atmospheric pressure to a pot volume of 4.68 vols. The batch was cooled to 70° C., heptane (2.02 vols) was added slowly drop-wise over at least 30 minutes maintaining the reaction temperature at 70±5° C. The mixture was cooled to 60° C., and seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide Form 1, agitated at 60° C. for 1 hour, cooled to 50° C. at 0.1° C., agitated at 50° C. for 140 minutes, then cooled to 22° C. at 0.1° C./minute. The mixture was held at 22° C. for at least 12 hours. Heptane (5.06 vols) was then added—drop-wise over at least 120 minutes maintaining the batch temperature at a temperature at 22±5° C. The mixture was cooled to 0° C. at 0.1° C./minute then held at 0° C. for at least 12 hours and then filtered. The isolated solid was washed with a mixture of methyl iso-butylketone (1.0 vols) and heptane (3.0 vols) pre-chilled to 0° C. The solid was dried at 40° C. After drying in the vacuum oven at 40° C. overnight, the desired product was obtained as a solid (corrected yield 85%. $^1$H NMR δ (400 MHz DMSO) 11.04 (s, 1H), 9.26 (s, 1H), 8.68 (s, 1H), 8.57 (s, 1H), 8.36 (s, 1H), 7.56 (s, 1H), 7.46 (s, 1H), 7.12 (s, 1H), 4.81-4.77 (m, 1H), 4.58-4.54 (t, 2H), 4.11-4.07 (t, 2H), 3.55-3.47 (m, 2H), 3.3 (s, 3H), 2.48 (s. 3H), 2.34-2.26 (m, 2H), 1.26-1.25 (d, 3H)

3-{[5-(Azetidin-1-ylcarbonyl)pyrazin-2-yl]oxy}-5-[(1S)-2-methoxy-1-methylethoxy]-N-(5-methylpyrazin-2-yl)benzamide

B

3-{[5-(Azetidin-1-ylcarbonyl)pyrazin-2-yl]oxy}-5-[(1S)-2-methoxy-1-methylethoxy]-benzoic acid (1.0 eq), (1.00 mol eq), 5-methylpyrazin-2-amine (1.12 mol eq) and 2-methyltetrahydrofuran (2.00 rel vols) were charged to a vessel and stirred at 20° C. N-methylmorpholine (5.00 mol eq) was added followed by a line-wash with 2-methyl-tetrahydrofuran (0.50 rel vols). A 50 wt % solution of 1-propanephosphonic acid cyclic anhydride (T3P) in 2-methyltetrahydrofuran (1.70 mol eq) was charged followed by a line wash with 2-methyltetrahydrofuran (0.50 rel vols). The resulting mixture was heated to 78° C. over 30 minutes and the clear yellow solution was held at 78° C. for roughly 22 hours, then checked for acceptable conversion. At the end of reaction the solution was further diluted with 2-methyltetrahydrofuran (7.00 rel vols) and the temperature was adjusted to 45° C. 5 wt % aq. sodium bicarbonate solution (6.00 rel vols) was slowly added over 30 mins to the stirring solution causing gas evolution. After 15 minutes stirring was turned off and the phases were allowed to separate over 30 minutes. The lower aqueous phase was drained off 20 wt % aq. phosphoric acid (3.30 rel vols) was charged to the stirring organic phase. After 15 minutes stirring the phases were allowed to separate and the lower aqueous phase was drained off again. A mixture of 20 wt % aq. phosphoric acid (1.50 rel vols) and water (1.50 rel vols) was charged to the stirring organic phase. After 15 minutes, stirring was turned off and the mixture held overnight for phase separation. The lower (aqueous) phase was drained off again. 5 Wt % aq. sodium bicarbonate (4.50 rel vols) was added over at least 10 mins to the stirring solution. After phase separation the lower (aqueous) phase was run off again. The resulting solution was dried by azeotropic distillation to a concentration of approximately 241 mg/g, collecting around 0.48 rel vols of the lower distillate phase. Heptane (1.60 rel vols) was added over 10 mins to the dry solution at above 50° C. before the batch was cooled to 40° C. The solution was seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide (Form 1 Seed, 0.0010 rel wt) before an overnight temperature program was applied: held at 40° C. for 2 hrs; cooled to 35° C. at 0.1° C./min (50 minutes); held for 2 hours; cooled to 30° C. at 0.1° C./min (50 minutes); held for 2 hours; cooled to 0° C. at 0.1° C./min (300 minutes); and held for at least 2 hours. After crystallisation overnight, further heptane (4.1 rel vols) was added over 2.0 hours to reduce losses to liquors to <4.0 mg/mL. The suspension was then filtered followed by a line rinse with a premixed solution of heptane (2.10 rel vols) and 2-methyltetrahydrofuran (0.90 rel vols) and transferred to a filtration apparatus. The filter cake was dried to constant weight at 40° C. to furnish crude 3-{[5-(azetidin-1-ylcarbonyl)pyrazin-2-yl]oxy}-5-[(1S)-2-methoxy-1-methylethoxy]-N-(5-methylpyrazin-2-yl)benzamide in 86-89% as Form I.

Process for Crystallisation of 3-{[5-(azetidin-1-ylcarbonyl)pyrazin-2-yl]oxy}-5-[(1S)-2-methoxy-1-methylethoxy]-N-(5-methylpyrazin-2-yl)benzamide (as form 4) from 2-methyltetrahydrofuran/isohexane To a flask fitted with overhead stirrer, condenser, thermometer and nitrogen line was added a solution of 3-{[5-(azetidin-1-ylcarbonyl)pyrazin-2-yl]oxy}-5-[(1S)-2-methoxy-1-methylethoxy]-N-(5-methylpyrazin-2-yl)benzamide in 2-methyltetrahydrofuran under a nitrogen atmosphere. The solution was distilled at atmospheric pressure until a pot volume of 7 vols was obtained. Iso-hexane (3 vols) was added at 70° C., then cooled to 50° C. for 1 hour. The mixture was seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide (form 1) (5% wt/wt). The mixture was cooled to 0° C. at 0.1° C./minutes and left to agitate at 0° C. for at least 48 hours. The mixture was filtered and dried and left to dry on standing at 22° C. to give the title compound as an off white solid. Yield of isolated solid was 68% as form 4.

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

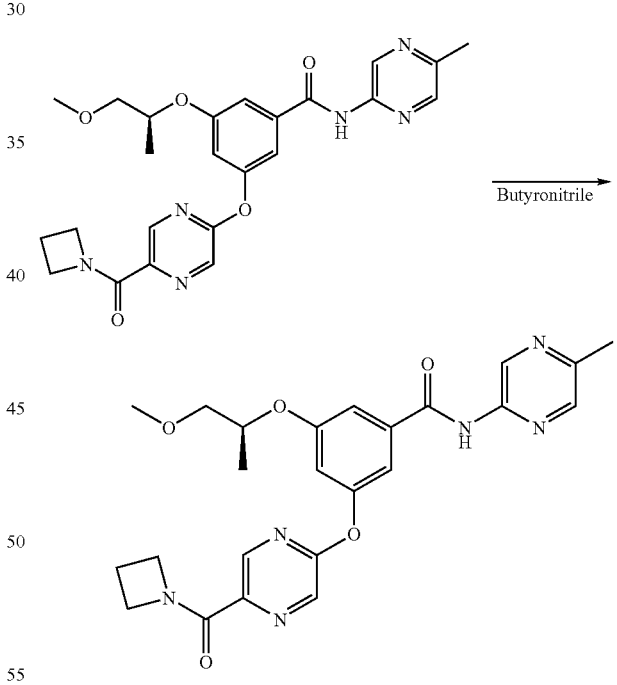

To a flask fitted with thermometer, condenser, overhead stirrer and nitrogen line was added 3-{[5-(azetidin-1-ylcarbonyl)pyrazin-2-yl]oxy}-5-[(1S)-2-methoxy-1-methylethoxy]-N-(5-methylpyrazin-2-yl)benzamide (1.0 eq) and butyronitrile (5.4 vols) under a nitrogen atmosphere. The batch was heated to 50° C. and filtered into another flask. The mixture was cooled to 45° C., and then seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide) (form 6) (0.075% w/w). The mixture was held at 45° C. for 3 hours, then cooled to 15° C. at 0.1° C./minute and held at 15°

C. for at least 24 hours then filtered. The solid was washed with butyronitrile (2 vols) pre-chilled to 15° C. The solid was dried at 40° C. until the solvent level was <0.5% w/w. After drying in the vacuum oven at 40° C. overnight, the title compound was obtained as a solid (corrected yield 85%).

Preparation of 5-Chloropyrazine-2-carboxylic acid

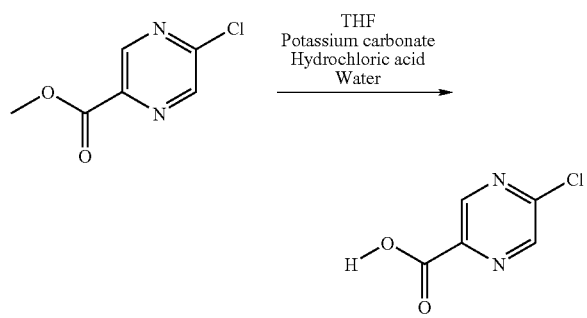

To a flask fitted with overhead stirrer, condenser, thermometer and nitrogen line was added methyl 5-chloropyrazine-2-carboxylate (1.0 eq) and tetrahydrofuran (4.92 vols) under a nitrogen atmosphere. The reaction mixture was agitated until all the solid had dissolved, then filtered into a second flask. Water (8.65 vols) was added to the reaction mixture and the mixture agitated for approximately 15 minutes. Potassium carbonate (2.1 eq) was added to the reaction mixture and the mixture agitated for 16 hours at 20-25° C. Then 32% w/w hydrochloric acid (3.76 eq) was added over 3 hours in small portions, keeping the reaction temperature 20-25° C., to a pH end point of pH2.2. The resultant slurry was heated to approximately 35-40° C. and then distilled under vacuum at this temperature distilling approximately 5.3 vols, to a final volume of approximately 9.3 vols. The mixture was then cooled to 20-25° C. over at least 2 hours, agitated for 10 hours at this temperature and then filtered. The solid was washed with water (2.8 vols), and the wet product produced dried at 35° C. in a vacuum oven. The desired product was obtained as a solid (corrected yield 91%) $^1$H NMR δ (400 MHz CDCl$_3$): 7.20 (1H, bs), 8.72 (1H, s), 9.21-9.21 (1H, m); m/z 157 (M-H)$^+$.

2-(Azetidin-1-ylcarbonyl)-5-chloropyrazine

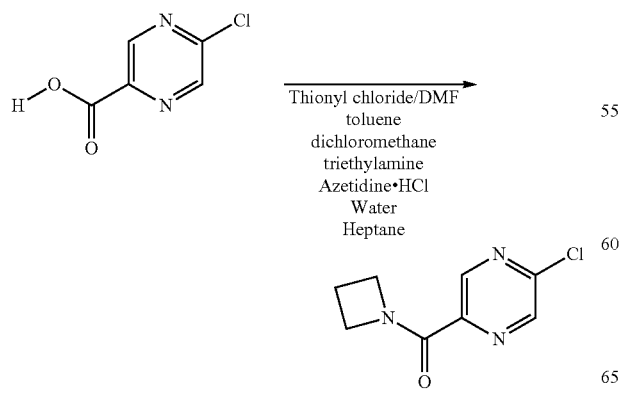

To a flask fitted with overhead stirrer, condenser, thermometer and nitrogen line was added 5-chloropyrazine-2-carboxylic acid (1.0 eq), DMF (0.069 eq) and toluene (5.52 vols) under a nitrogen atmosphere. The mixture was heated to 60-65° C., and thionyl chloride (1.5 eq) added drop-wise to the batch over approximately 2 hours. The thionyl chloride was washed into the flask with toluene (0.2 vols). The reaction mixture was heated at 60-65° C. for at least 4 hours, then cooled to 40-45° C. and distilled under vacuum, removing approximately 4.5 vol distillates, and distilling to a final volume of 3.2 vols. Toluene (10.6 vol) was added, and the mixture distilled under vacuum at 40-45° C., removing approximately 9.1 vol distillates, and distilling to a final volume of 4.7 vols. The mixture was then cooled to 20-25° C., and dichloromethane (10.6 vols) added. The mixture was cooled to 0-5° C. Meanwhile, to a second flask fitted with overhead stirrer, condenser, thermometer and nitrogen line was added azetidine hydrochloride (0.284 eq), dichloromethane (5.2 vols) under a nitrogen atmosphere. Triethylamine (2.57 eq) was added over at least 15 minutes maintaining the reaction temperature from 20-25° C., the triethylamine was washed into the flask with dichloromethane (0.13 vols), and the mixture cooled to −5° C. to −10° C. The acid chloride solution in the first flask was added to the second flask in portions maintaining the reaction temperature at −5° C. to −10° C. over a time period of 2-5 hours. The pH was tested and adjusted to pH>7 after the acid chloride addition. The reaction mixture was agitated for at least 30 minutes at −5° C. to −10° C. Water (10.6 vols) was added to the second flask and the temperature was allowed to increase to 20-25° C. The mixture was agitated for approximately 25 minutes and then the layers were separated. A 3.17% w/w solution (1.46 eq) of hydrochloric acid (prepared from 32% w/w hydrochloric acid and water) was added to the organic layer B keeping the batch temperature at 20-25° C. The mixture was agitated for 30 minutes at this temperature. The layers were separated, and the organic phase was treated with 26% w/w sodium chloride solution (approximately 8.9 vols) and the batch agitated at 20-25° C. for at least 15 minutes. The layers were separated and the organic layers was heated to reflux, and dichloromethane was removed by atmospheric distillation, distilling to a final volume of approximately 1-2 vols, collecting approximately 11.9 vols distillates. The resulting mixture was cooled to 20-25° C., and heptane (10.5 vols) added. The mixture was heated to reflux for 60 minutes, and then cooled to 90-100° C. The hot solution was filtered through a filter containing 10% w/w of activated charcoal into a clean dry vessel. The filter was washed with heptane (0.43 vols) and the solution cooled to 20-25° C. over at least 2 hours. The resulting crystallised slurry was filtered, and the solid washed with pentane (0.94 vols). After drying in the vacuum oven at 40° C. overnight, the desired product was obtained as a solid (corrected yield 65-78%). $^1$H NMR δ (400 MHz CDCl$_3$): 2.35-2.42 (2H, m), 4.26 (2H, t), 4.67 (2H, t), 8.52 (1H, d), 9.09 (1H, d); m/z 198 (M+H)$^+$.

tert-Butyl (5-methylpyrazin-2-yl)carbamate

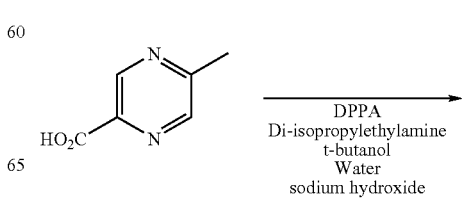

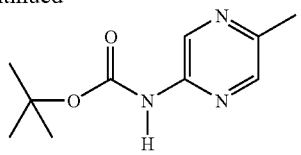

To a flask fitted with overhead stirrer, condenser, thermometer and nitrogen line was added 5-methylpyrazine-2-carboxylic acid (1.0 eq), tert-butanol (3.5 vols) and di-isopropylethylamine (1.5 eq) under a nitrogen atmosphere. The mixture was heated to 82° C., then diphenylphosphorylazide (1.0 eq) was added over a time period of 5-14 hours, maintaining the temperature of the reaction mixture at approximately 82° C. The reaction mixture was stirred for at least 1.5 hours, and then cooled to approximately 60° C. A solution of 4% w/w sodium hydroxide (1.75 eq) was added over a period of 2 hours. The mixture was cooled to 15° C. over at least 5 hours then held at 15° C. for 3 hours. The batch was then filtered, and the solid slurry washed with water (2 vols). The batch was again slurry washed with water (2 vols). After drying at 55-60° C. overnight, the desired product was obtained as a solid (corrected yield 56-63%). $^1$H NMR δ (400 MHz CDCl$_3$): 9.18 (s, 1H), 8.17 (bs, 1H), 8.11 (s, 1H), 2.51 (s, 3H), 1.56 (s, 9H)

5-Methylpyrazin-2-amine

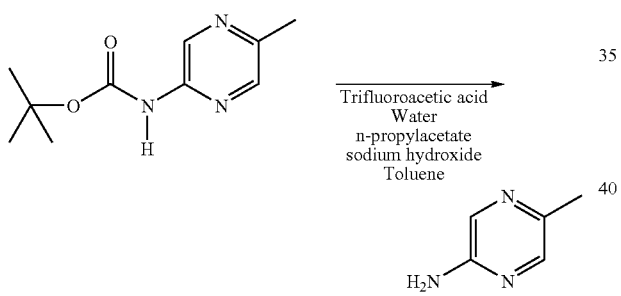

To a flask fitted with overhead stirrer, condenser, thermometer and nitrogen line was added tert-butyl (5-methylpyrazin-2-yl)carbamate (1.0 eq), and water (6.85 vols). The mixture was heated to 70° C. and trifluoroacetic acid (TFA) (1.2 eq) was added slowly drop-wise over 90-120 minutes. Water (0.22 vols) was added to wash the TFA into the flask. The reaction mixture was heated at 65-75° C. for at least 30 minutes, and then cooled to 15-25° C. Then 32% w/w sodium hydroxide (1.30 eq) was added drop-wise over 30-60 minutes maintaining the reaction temperature between 15-40° C. Water (0.22 vols) was added to wash the sodium hydroxide into the flask. N-Propylacetate (7.0 vols) was added and the mixture agitated for 45 minutes at 20° C. The layers were separated, the organic layer was retained and the aqueous layer was returned to the flask. N-Propylacetate (7.0 vols) was added and the mixture agitated for 45 minutes at 20° C. The layers were separated, the organic layer was retained and the aqueous layer was returned to the flask. This process was repeated twice. The combined organic layers were filtered through a filter containing silica (20% w/w) into a clean dry flask. The mixture was heated to 40° C. and then vacuum distilled to a final volume of 1.0-1.33 vols. Toluene (3.0 vols) was added, and the vacuum distillation continued at 40° C. to a final volume of 1.0-1.33 vols. This process was repeated twice. The resulting mixture was cooled to 5° C., and agitated for 1 hour at this temperature then filtered, washed with toluene (0.3 vols) at 0-5° C. The batch is slurry washed with toluene (1.0 vol) at 0-5° C. After drying at 45° C. overnight, the desired product was obtained as a solid (corrected yield typically 75%). $^1$H NMR δ (400 MHz CDCl$_3$): 7.92 (s, 1H), 7.87 (s, 1H), 4.6 (bs, 2H), 2.40 (s, 3H)

Preparation of methyl 3-{[5-(azetidin-1-ylcarbonyl)pyrazin-2-yl]oxy}-5-[(1S)-2-methoxy-1-methylethoxy]benzoate

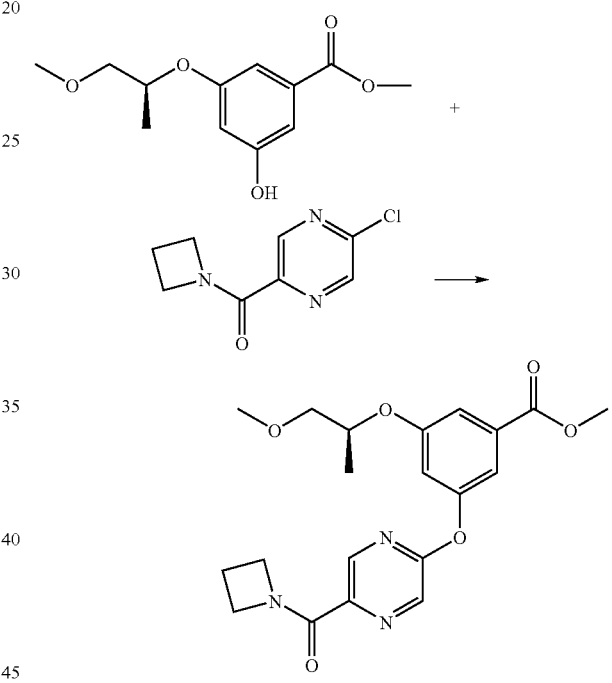

To a flask fitted with overhead stirrer, condenser, thermometer and nitrogen line was added methyl 3-hydroxy-5-[(1S)-2-methoxy-1-methylethoxy]benzoate (1.0 eq), 2-(azetidin-1-ylcarbonyl)-5-chloropyrazine (1.05 eq), cesium carbonate (1.5 eq) and dimethylsulfoxide (10 vols) under a nitrogen atmosphere. The contents of the flask were heated to 45° C. for 1.5 hours, then cooled to 22° C. Ethyl acetate (6 vols) and water (6 vols) were added to the flask, the mixture was agitated for 15 minutes, then the layers were separated. Water (3 vols) was added to the organic layer, the batch agitated for 15 minutes, then the layers were separated. This process was repeated with water (3 vols) then saturated brine (6 vols), then with water (6 vols). The organic layer was evaporated on the rotary evaporator to yield the title compound as an oil (93% yield corrected for assay). $^1$H NMR δ (400 MHz) DMSO: 8.62 (s, 1H), 8.50 (s, 1H), 7.34 (s, 1H), 7.30 (s, 1H), 7.17 (s, 1H), 4.68-4.64 (m, 1H), 4.54-4.49 (t, 2H), 4.07-4.03 (t, 2H), 3.81 (s, 3H), 3.49-3.41 (m, 2H), 3.25 (s, 3H), 2.29-2.22 (m, 2H), 1.20-1.18 (d, 3H).

3-{[5-(Azetidin-1-ylcarbonyl)pyrazin-2-yl]oxy}-5-[(1S)-2-methoxy-1-methylethoxy]-N-(5-methylpyrazin-2-yl)benzamide

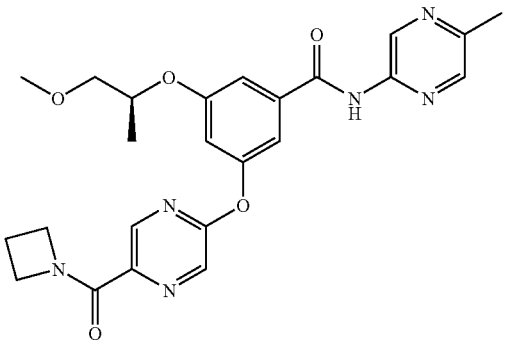

To a flask fitted with overhead stirrer, condenser, thermometer and nitrogen line was added 3-{[5-(azetidin-1-ylcarbonyl)pyrazin-2-yl]oxy}-5-[(1S)-2-methoxy-1-methylethoxy]benzoic acid (1.0 eq), and acetonitrile (10 vols) followed by pyridine (3 eq) under a nitrogen atmosphere. Thionyl chloride (1.2 eq) as a solution in acetonitrile (0.225 vols) was added slowly, drop-wise via syringe pump over at least 2 hours. 5-Methylpyrazin-2-amine (1.2 eq) was added to the mixture as a solid. After 2.5 hours the reaction was quenched by adding toluene (10 vols) and 1.0M sodium carbonate solution (2.5 eq). The layers were separated. The organic layer was retained in the flask, then 1.0M hydrochloric acid (1.94 eq) was added. The mixture was agitated for 15 minutes then separated. The organic layer was washed with two aliquots of water (5 vols) then the solvent was removed on the rotary evaporator. Toluene (5 vols) was added to the residue, and warmed to 45° C. Isohexane (1.7 vols) was added, the mixture was seeded, and allowed to cool to ambient temperature overnight. The mixture was cooled to 0° C. for 4 hours, and then cooled to −10° C. for 3 hours. The solid was isolated by filtration then washed with iso-hexane (2.5 vols). After drying in the vacuum oven at 40° C. overnight, the desired product was obtained as a solid (corrected yield 85%).

2-(Azetidin-1-ylcarbonyl)-5-chloropyrazine

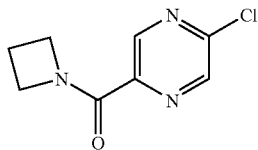

To a flask fitted with overhead stirrer, condenser, thermometer and nitrogen line was added 5-chloropyrazine-2-carboxylic acid (1.0 eq), tetrabutylammonium chloride (0.011 eq) and toluene (4 vols) under a nitrogen atmosphere. The mixture was heated to 70-75° C., and thionyl chloride (1.35 eq) added drop-wise over approximately 1 hours. The thionyl chloride was washed into the flask with toluene (1 vol). The mixture was heated at 70-75° C. for at least 4 hours, then cooled to 50±5° C. Toluene (5.3 vols) was added, and the mixture vacuum distilled at 50±5° C. (100 mbar), removing approximately 5.3 vol distillates, and distilling to a final volume of 5 vols. This process was repeated. The resulting mixture was then cooled to 20-25° C. Toluene (8.93 vols) was added, and the batch agitated at 50±5° C. to give an acid chloride solution.

Meanwhile, to a second flask was added azetidine hydrochloride (1.05 eq), toluene (6.07 vols), and a solution of potassium carbonate (1.24 eq) in water (6.07 vols). The resulting mixture was agitated at 20±5° C. for at least 15 minutes, then the layers were separated. The aqueous layer was returned to the flask, and toluene (6.07 vols) was added. The mixture was agitated at 20±5° C. for at least 15 minutes, then the layers were separated. The aqueous layer was returned to the flask, and potassium carbonate (1.24 eq) and toluene (6.07 vols) were added. The mixture was agitated for at least 30 minutes The acid chloride solution in the first flask was added to the mixture in the second flask in portions maintaining the reaction temperature at 20±5° C. over a time period of at least 20-60 minutes. The reaction mixture was agitated for at least 30 minutes at 20±5° C. and then filtered, the filter was washed with toluene (0.17 vol) and then the layers were separated. The lower aqueous phase was separated off and discarded. Water (6.07 vols) was added to the second flask and the mixture was agitated at 20±5° C. for approximately 15 minutes and then allowed to separate. The lower aqueous phase was separated off and discarded. A 5% w/w solution of hydrochloric acid (1.5 eq) (prepared from 32% w/w hydrochloric acid and water was added to the organic layer keeping the batch temperature at 20±5° C. The mixture was agitated for 15 minutes at this temperature then the layers were separated and the lower aqueous layer was discarded. 25% w/w Sodium chloride solution (approximately 6 vols) was added to the organic layer and the mixture agitated at 20-25° C. for at least 15 minutes. The layers were separated and the aqueous layer was discarded. The organic layer was heated to 50±5° C., and vacuum distilled to a final volume of 4.5 vols, collecting 15.2 vols distillate. Active charcoal (11% w/w) and heptane (12.8 vols) were added, and the mixture agitated at 90-100° C. for at least 1 hour. The mixture was filtered to clean dry vessel keeping the reaction temperature above 70° C.

Heptane (1.16 vols) was used to wash the mixture into the filter. The mixture was cooled to 55-60° C., seeded with 2-(azetidin-1-ylcarbonyl)-5-chloropyrazine and cooled to 15-20° C. over at least 3 hours. The crystallised slurry was filtered, and the solid washed with 140-155 petroleum ether (1.45 vols). The solid was washed with 140-155 petroleum ether (1.45 vols). After drying in the vacuum oven at 40° C. overnight, the desired product was obtained as a solid corrected yield 65-78%).

Benzyl (5-methylpyrazin-2-yl)carbamate

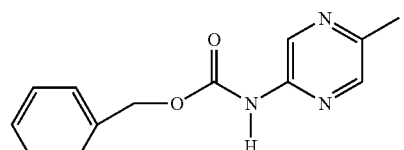

To a flask fitted with overhead stirrer, condenser, thermometer and nitrogen line was added 5-methylpyrazine-2-carboxylic acid (1.0 eq), toluene (2.5 vols) and di-isopropylethylamine (1.50 eq) under a nitrogen atmosphere. The mixture was vacuum distilled at a batch temperature of 50° C., distilling to a final volume of 2 vols. The batch was sampled to ensure the water content was <0.1% w/w, then cooled to 15±2° C., and diphenylphosphorylazide (1.00 eq) was added over a time period of 5-6 hours, maintaining the temperature of the reaction mixture at 15±2° C. The mixture was stirred for a further 1.5 hours. Meanwhile to a second flask was added benzyl alcohol (3.00 eq) and toluene (11 vols). The mixture was azeotropically dried to a volume of 10 vols. The contents of the second flask were sampled to ensure the water content was <0.1% w/w, then heated to 85-90° C. The contents of the first flask were added slowly to the contents of the second flask over approximately 2 hours, maintaining the reaction temperature at approximately 85° C. The reaction mixture was stirred for 1 hour at 85° C., then cooled to 20° C. 5% w/w Sodium hydroxide solution (1.75 eq) was added slowly over 1 hour, the mixture cooled to 5° C., agitated at 5° C. for 1 hour, then filtered. The isolated solid was washed sequentially with water (2 vols), then methanol (2 vols). After drying in the vacuum oven at 40° C. overnight, the desired product was obtained as a solid (corrected yield 78-85%). $^1$H NMR (400 MHz, CDCl$_3$): 9.41 bs (1H), 9.24 s (1H), 7.87 s (1H), 7.39-7.41 m (5H), 5.22 s (2H), 2.31 s (3H)

5-Methylpyrazine-2-amine

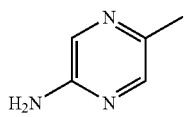

To a flask fitted with overhead stirrer, condenser, thermometer and nitrogen line was added benzyl(5-methylpyrazin-2-yl)carbamate (1.0 eq), palladium on carbon catalyst E196 (3% w/w palladium on dry basis)), sodium hydroxide (0.01 eq)- and methanol (5 vols) under a nitrogen pad. The reaction was de-gassed by pressurising and releasing under nitrogen, then charged with hydrogen to atmospheric pressure and the reaction agitated at 20±5° C. for at least 3 hours. Activated charcoal (Norit SX Ultra) (5% wt charge) was added to the flask, the mixture was agitated for at least 30 minutes at 20±5° C., then filtered through a 0.45 micron filter. The filter was rinsed with methanol (1 vol) then the mother liquors allowed to stir at 15° C. under an atmosphere of 6% oxygen/94% nitrogen for up to 24 hours (alternatively an atmosphere of 1% oxygen/99% nitrogen was used), then re-filtered through the 0.45 micron filter. The mother liquors were vacuum distilled at 45° C. to a final volume of 1.5 vols. Toluene (1.5 vols) was added and the mixture vacuum distilled at 45° C. to a final volume of 1.5 vols. This process was repeated with further toluene (0.5 vols) then the resulting mixture was cooled to 5° C. and filtered. The solid was washed with toluene (1 vol). The solid was washed with toluene (1 vol). After drying in the vacuum oven at 40° C. overnight, the desired product was obtained as a solid (corrected yield 65-78%).

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

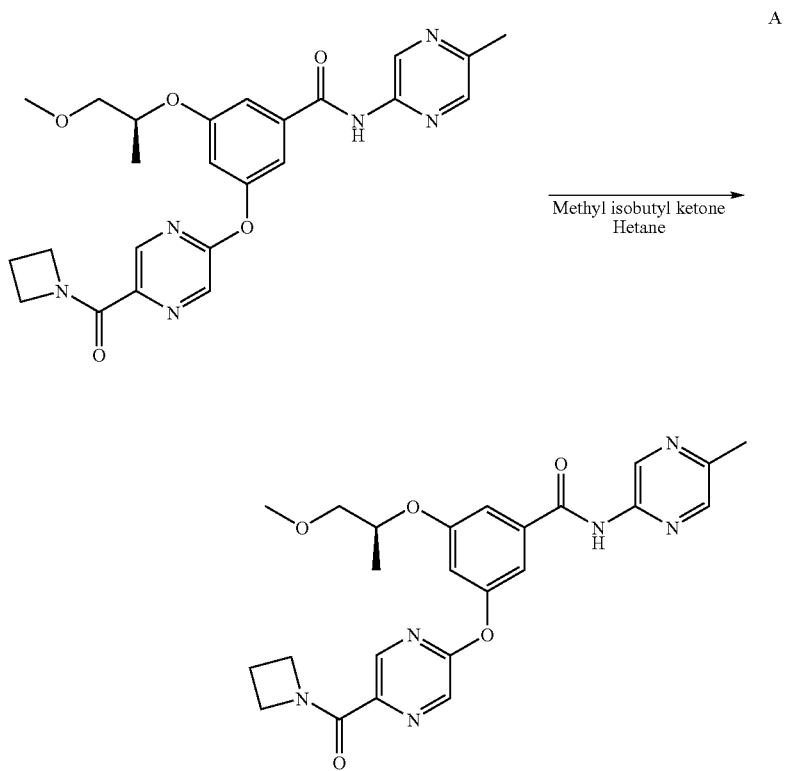

To a flask fitted with thermometer, condenser, overhead stirrer and nitrogen line was added 3-{[5-(azetidin-1-ylcarbonyl)pyrazin-2-yl]oxy}-5-[(1S)-2-methoxy-1-methylethoxy]-N-(5-methylpyrazin-2-yl)benzamide (1.0 eq) and methyl isobutyl ketone (6.7 vols) under a nitrogen atmosphere. The batch was heated to 60° C. and filtered into another flask. The mixture was cooled to 45° C., and then seeded with 3-{[5-(azetidin-1-ylcarbonyl)pyrazin-2-yl]oxy}-5-[(1S)-2-methoxy-1-methylethoxy]-N-(5-methylpyrazin-2-yl)benzamide) (form 6) (0.075% w/w). The mixture was held at 45° C. for 6 hours, then subjected to a stepped cooling profile. The mixture was cooled to 40° C. and held for 6 hours, then cooled to 35° C. and held for 6 hours, then cooled to 30° C. and held for 6 hours, then cooled to 20° C. and held for 6 hours, then cooled to 10° C. and held for 3 hours. To the mixture n-heptane was then added slowly over a period of 2 hours maintaining the mixture at 10° C., following the addition the mixture was held for a further 1 hour at 10° C. The mixture was then cooled to 0° C. and held for 6 hours before being filtered. The solid was washed with (2 vols) methyl isobutyl ketone/n heptane mixture (9/1 volume ratio) pre-chilled to 0° C. The solid was dried at 40° C. until the solvent level was <0.5% w/w. After drying in the vacuum oven at 40° C. overnight, the title compound was obtained as a solid (corrected yield 85%).

Preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide) (as form 6)

B

Crude 3-{[5-(azetidin-1-ylcarbonyl)pyrazin-2-yl]oxy}-5-[(1S)-2-methoxy-1-methyl-ethoxy]-N-(5-methylpyrazin-2-yl)benzamide) was suspended in 6.7 rel vol. of methyl isobutyl ketone (MIBK). The mixture was heated to 70° C. to dissolve the solid. Once the solid has dissolved the mixture was filtered to generate a Pures envelope. The solution was then cooled to 45° C., seeded with 3-{[5-(azetidin-1-ylcarbonyl)pyrazin-2-yl]oxy}-5-[(1S)-2-methoxy-1-methyl-ethoxy]-N-(5-methylpyrazin-2-yl)benzamide) Form VI and held for 4 hours at 45° C. The mixture was then cooled using a stepped cooling profile (cooled to 40° C. and held for 4 hours, cooled to 35° C. and held for 6 hours, cooled to 30° C. and held for 6 hours cooled to 20° C. and held for 3 hours, cooled to 10° C. and held for 3 hours and cooled to 0° C. and held for 3 hours). The mixture was then subjected to a number of temperature cycles to break up the crystal agglomerates. The mixture was heated from 0° C. to 30° C. at 0.5° C./min, and held at 30° C. for 2 hours and then cooled back to 0° C. at 0.1° C./min and held at for 3 hours. This temperature cycle was repeated a further 3 times. After an in-process control to confirm the formation of the desired physical form, the mixture was filtered and washed with 50/50 v/v MIBK/n-heptane. The solid was dried under vacuum at 60° C. until constant weight was attained. Yield=75-82%.

Alternatively, the crystallisation may be performed as described above but with the assistance of an ultrasonic probe to achieve the desired particle size. Wet milling may also be used to achieve the required particle size reduction.

It will be appreciated by those skilled in the art that the sequence of steps in the processes described above may be performed in a different order for example 3-hydroxy-5-[(1S)-2-methoxy-1-methylethoxy]benzoic acid may be reacted with 5-methylpyrazine-2-amine to give (S)-3-hydroxy-5-(1-methoxypropan-2-yloxy)-N-(5-methylpyrazin-2-yl)benzamide, for example as described below. The conversion of (S)-3-hydroxy-5-(1-methoxypropan-2-yloxy)-N-(5-methylpyrazin-2-yl)benzamide into 3-{[5-(azetidin-1-ylcarbonyl)pyrazin-2-yl]oxy}-5-[(1S)-2-methoxy-1-methylethoxy]-N-(5-methylpyrazin-2-yl)benzamide may be carried out as described in WO2007/007041.

Synthesis of (S)-3-hydroxy-5-(1-methoxypropan-2-yloxy)-N-(5-methylpyrazin-2-yl)benzamide

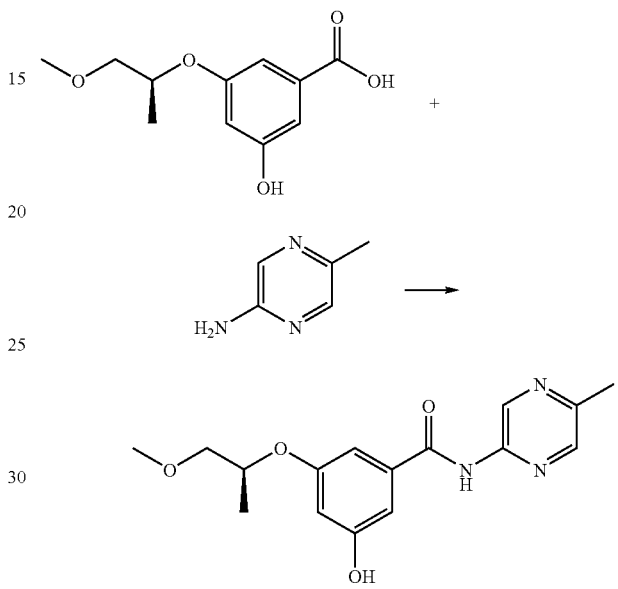

To a clean dry flask was added 3-hydroxy-5-[(1S)-2-methoxy-1-methylethoxy]benzoic acid (1.0 mol eq), tetrabutylammonium chloride (0.01 eq), and toluene (10 L/kg). Thionyl chloride (1.5 eq) was added in one go and the reaction heated to 60° C. for 2 hours. The reaction mixture was distilled to an oil at 40° C. on the rotary evaporator, and acetonitrile (4 L/kg) added.

To a second clean dry flask was added 5-methylpyrazine-2-amine (1.0 mol eq), pyridine (3.0 mol eq) and acetonitrile (4 L/kg). The acid chloride solution was added to the amine solution over 30 minutes at 22° C. and then allowed to agitate overnight.

The reaction mixture was distilled to an oil at 40° C. on the rotary evaporator, and toluene (4 L/kg) added. The reaction mixture was distilled to give an oil at 40° C. on the rotary evaporator, then toluene (10 L/kg added) followed by water (4 L/kg) and 1.0M hydrochloric acid (4 L/kg). The reaction mixture was agitated at 22° C. for 30 minutes, whereupon it crystallized, and toluene (4 L/kg) and water (4 L/kg) was added.

The reaction mixture was filtered and washed sequentially with water 2×(2 L/kg), then toluene 2×(2 L/kg).

The filtrate was agitated overnight at 22° C. and further crystallisation was observed. The reaction mixture was filtered. The solids were dried to give the title compound as an off-white solid in 35% yield.

$^1$H NMR δ (400 MHz DMSO) 10.86 (bs, 1H), 9.75 (bs, 1H), 9.25-9.24 (s, 1H), 9.35 (s, 1H), 6.99 (t, 1H), 6.81 (t, 1H), 6.53-6.52 (t, 1H), 4.72-4.65 (m, 1H), 3.52-3.43 (m, 2H), 3.30 (s, 3H), 2.48 (s, 3H), 1.24-1.22 (d, 3H).

Synthesis of (S)-3-hydroxy-5-(1-methoxypropan-2-yloxy)-N-(5-methylpyrazin-2-yl)benzamide

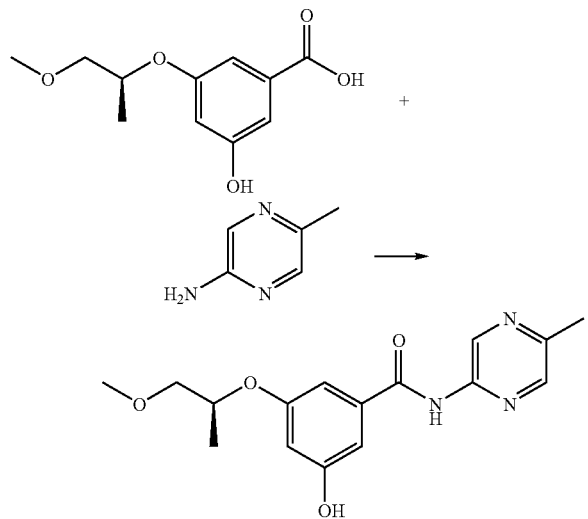

3-Hydroxy-5-[(1S)-2-methoxy-1-methylethoxy]benzoic acid (1.0 mol eq), tetrabutylammonium chloride (0.1 mol eq), and toluene (5 L/kg), were added to a flask and then thionyl chloride (1.35 mol eq) was added drop-wise to the reaction mixture at 22° C. The reaction mixture was heated at 35° C. for 2 hours, then warmed at 40° C. for 1.5 hours. The reaction mixture was distilled at 40° C. on the rotary evaporator to an oil, and then acetonitrile (5 L/kg) was added to the residue.

5-Methylpyrazine-2-amine (1.0 mol eq), pyridine (3.0 mol eq) and acetonitrile (5 L/kg) were added to a second flask and this solution was cooled to 5° C. The acid chloride solution was added to the amine solution over 1 hour maintaining the reaction temperature at <10° C. The mixture was then agitated overnight and warmed up to 22° C.

The reaction mixture was quenched by the addition of saturated sodium chloride solution and the resultant brine layer was then separated off and the organic layer was distilled to an oil at 40° C. on the rotary evaporator, and then toluene (7.5 L/kg) and water (2.5 L/kg) were added. The reaction mixture was cooled to 5° C., and 1M sodium hydroxide (1.0 eq) added drop-wise. The solution was agitated at 5° C. for 1 hour and the organic layer separated off. 2M Hydrochloric acid was added drop-wise at 5° C. until pH4.3 was attained. The reaction mixture was filtered, washed with 2× water (4 L/kg) and then dried in a vacuum oven at 40° C. until constant weight was achieved. The solids were dried to give the title compound as a tan solid in 61.5% yield corrected for assay.

$^1$H NMR δ (400 MHz DMSO) 10.86 (bs, 1H), 9.75 (bs, 1H), 9.25-9.24 (s, 1H), 9.35 (s, 1H), 6.99 (t, 1H), 6.81 (t, 1H), 6.53-6.52 (t, 1H), 4.72-4.65 (m, 1H), 3.52-3.43 (m, 2H), 3.30 (s, 3H), 2.48 (s, 3H), 1.24-1.22 (d, 3H).

The invention claimed is:

1. A process for the preparation of 3-{[5-(azetidin-1-ylcarbonyl)pyrazin-2-yl]oxy}-5-[(1S)-2-methoxy-1-methylethoxy]-N-(5-methylpyrazin-2-yl)benzamide comprising
   reacting 3-{[5-(azetidin-1-ylcarbonyl)pyrazin-2-yl]oxy}-5-[(1S)-2-methoxy-1-methylethoxy]benzoic acid with 5-methylpyrazin-2-amine in the presence of
   a solvent,
   a base and
   1-propanephosphonic acid cyclic anhydride.

2. The process according to claim 1 wherein the solvent is 2-methyltetrahydrofuran.

3. The process according to claim 1 wherein the base is N-methylmorpholine.

* * * * *